United States Patent
Min et al.

(10) Patent No.: US 12,421,393 B2
(45) Date of Patent: Sep. 23, 2025

(54) PROBE FOR DETECTING CARBAPENEM-RESISTANT BACTERIA AND USE THEREOF

(71) Applicant: INDUSTRY-UNIVERSITY COOPERATION FOUNDATION HANYANG UNIVERSITY ERICA CAMPUS, Ansan-si (KR)

(72) Inventors: Sun Joon Min, Seoul (KR); Yeon Joon Park, Seoul (KR); Ju Hyeon Kim, Boryeong-si (KR)

(73) Assignee: INDUSTRY-UNIVERSITY COOPERATION FOUNDATION HANYANG UNIVERSITY ERICA CAMPUS, Ansan-si (KR)

( * ) Notice: Subject to any disclaimer, the term of this patent is extended or adjusted under 35 U.S.C. 154(b) by 1005 days.

(21) Appl. No.: 17/260,622

(22) PCT Filed: Jul. 30, 2019

(86) PCT No.: PCT/KR2019/009495
§ 371 (c)(1),
(2) Date: Jan. 15, 2021

(87) PCT Pub. No.: WO2020/027553
PCT Pub. Date: Feb. 6, 2020

(65) Prior Publication Data
US 2021/0277246 A1    Sep. 9, 2021

(30) Foreign Application Priority Data

Aug. 3, 2018 (KR) .................. 10-2018-0090739
May 27, 2019 (KR) .................. 10-2019-0061630

(51) Int. Cl.
| | | |
|---|---|---|
| C07D 487/04 | (2006.01) | |
| C09B 19/00 | (2006.01) | |
| C09B 57/00 | (2006.01) | |
| C09B 57/02 | (2006.01) | |
| C09K 11/06 | (2006.01) | |
| C12Q 1/34 | (2006.01) | |

(52) U.S. Cl.
CPC ............ *C09B 19/00* (2013.01); *C07D 487/04* (2013.01); *C09B 57/00* (2013.01); *C09B 57/02* (2013.01); *C09K 11/06* (2013.01); *C12Q 1/34* (2013.01)

(58) Field of Classification Search
CPC ........ C07D 487/04; C09B 57/00; C09B 57/02
See application file for complete search history.

(56) References Cited

U.S. PATENT DOCUMENTS

2021/0207188 A1*    7/2021 Yang .................. C12Q 1/34

FOREIGN PATENT DOCUMENTS

| CN | 106279178 A | 1/2017 |
|---|---|---|
| KR | 10-1829453 B1 | 2/2018 |
| WO | WO 99/62907 A1 | 12/1999 |
| WO | WO 2016/188998 A1 | 12/2016 |
| WO | WO 2017/158616 A1 | 9/2017 |

OTHER PUBLICATIONS

Mao, Wuyu, et al., "Detection of Carbapenemase-Producing Organisms with a Carbapenem-Based Fluorogenic Probe," *Angewandte Chemie*, 129, 16, 2017 (pp. 4539-4543).
International Search Report issued on Nov. 29, 2019 in counterpart International Patent Application No. PCT/KR2019/009495 (4 pages in English and 4 pages in Korean).
Written Opinion issued on Nov. 29, 2019 in counterpart International Patent Application No. PCT/KR2019/009495 (8 pages in Korean).

* cited by examiner

*Primary Examiner* — Laura L Stockton
(74) *Attorney, Agent, or Firm* — NSIP Law

(57) ABSTRACT

The present disclosure relates to a compound represented by Chemical Formula 1, a probe for detecting antibiotic-resistant bacteria, which includes the compound, a composition containing the compound, a kit including the compound and a method for detecting antibiotic-resistant bacteria. A compound probe having a carbapenem structure and including a linker and a fluorophore can detect beta-lactamase or carbapenemase at high sensitivity and, therefore, can be applied to various biochemical researches. In addition, the compound probe can clinically detect carbapenemase-producing antibiotic-resistant bacteria and allows molecular diagnosis of antibiotic-resistant bacterial infectious diseases and analysis of antibiotic-resistant bacteria from a target sample at high sensitivity. Therefore, it can be effectively used for medicinal uses such as in-vitro diagnosis.

2 Claims, No Drawings

PROBE FOR DETECTING CARBAPENEM-RESISTANT BACTERIA AND USE THEREOF

CROSS REFERENCE TO RELATED APPLICATION(S)

This application is a U.S. National Stage Application of International Application No. PCT/KR2019/009495, filed on Jul. 30, 2019. This application and PCT/KR2019/009495 claim the benefit under 35 USC 119 (a) and 365 (b) of Korean Patent Application Nos. 10-2018-0090739 filed on Aug. 3, 2018 and 10-2019-0061630 filed on May 27, 2019 in the Korean Intellectual Property Office.

TECHNICAL FIELD

The present disclosure relates to a compound represented by Chemical Formula 1, a probe for detecting antibiotic-resistant bacteria, which includes the compound, a composition containing the compound, a kit including the compound and a method for detecting antibiotic-resistant bacteria.

BACKGROUND ART

The emergence of antibiotic-resistant bacteria has brought about threat to public health. One of the most general mechanisms of the resistance is the expression of a specific enzyme capable of cleaving β-lactam ring of an antibiotic, which results in loss of the activity of the drug.

A carbapenem antibiotic is an antibiotic having a β-lactam ring. It exhibits a broad spectrum of antibacterial activity and has been used as a therapeutic agent for severe bacterial infection since 1980s due to stability against beta-lactamase.

However, with the widespread use of the carbapenem antibiotic, the emergence of carbapenem antibiotic-resistant bacteria is increasing recently. It has been found out that Gram-negative bacteria exhibiting resistance to the carbapenem antibiotic express carbapenemase, which is a carbapenem β-lactamase, in vivo.

As the carbapenemases, 9 varieties belonging to the class A according to Ambler's classification, including the most common KPC, 6 varieties belonging to the class B including NDM and VIM, and 2 varieties belonging to the relatively scarce class D including OXA-48, are known.

At present, it is very difficult to detect carbapenemase-producing bacteria because the degree of drug resistance varies depending on the type of the carbapenemase the drug-resistant bacteria have. Accordingly, prior to the time-consuming and costly development of next-generation antibiotics for treating the drug-resistant bacteria, a method for detecting antibiotic-resistant bacteria early and sensitively is essential to effectively control the diffusion of carbapenemase and adequate cope with it.

At present, there are two types of methods for quickly and effectively detecting carbapenemase-expressing bacteria: (1) phenotyping assay and (2) genotyping assay.

The phenotyping assay involves modified Hodge test of observing whether indicator bacteria *E. coli* grow toward the inoculated bacteria due to carbapenem secreted by the tested bacteria and double-disk synergy test of inhibiting carbapenemase activity by adding a specific carbapenemase inhibitor.

However, because this method lacks specificity and sensitivity and time (24-48 hours) is required for bacterial growth, it is not appropriate for timely provision of data necessary to select an antibiotic for a patient requiring fast treatment, e.g., sepsis.

The genotyping assay is based on detection by polymerase chain reaction (PCR). Although this method, wherein the positivity for the carbapenemase gene is investigated using primers specific for the gene, has high accuracy and sensitivity, there are disadvantages that it is costly, is applicable only to the detection of previously known genotypes and requires skilled personnel.

In order to overcome those disadvantages, a method capable of detecting the presence of carbapenemase-expressing antibiotic-resistant bacteria more accurately and effectively is urgently needed in the art.

Recently, a probe capable of detecting cefotaxime-resistant bacteria was developed using cefotaxime of the cephalosporin family as a backbone and BODIPY as a fluorophore (Korean Patent Registration No. 10-1829453 (Jan. 25, 2017)). In addition, CPC-1 having the beta-lactam backbone of carbapenem with the hydroxycoumarin fluorophore bound (Chinese Patent Publication No. 106279178A (Jan. 4, 2017)) is capable of metallo-beta-lactamases (VIM-1, NDM-1, IMP-1, etc.) from among carbapenemases. However, the CPC-1, which has a structure wherein the carbapenem portion and the fluorophore are bound directly, has problems that the synthesis procedure is uneconomical because a reaction for reducing the number of carbons is necessary for the synthesis of an intermediate compound and that it cannot be used for early detection of carbapenem-resistant bacteria with high sensitivity and reliability because only metallo-beta-lactamases cannot be detected selectively.

The inventors of the present disclosure have made consistent efforts to develop a probe which can detect carbapenemase with high sensitivity, thus being applicable to various biochemical researches, can clinically detect antibiotic-resistant bacteria which cannot be detected with the existing pH indicator-based method, and allows molecular diagnosis of antibiotic-resistant bacterial infectious diseases and analysis of antibiotic-resistant bacteria from a target sample with high sensitivity. As a result, they have identified that a broad spectrum of carbapenem-resistant bacteria can be detected with high sensitivity by contacting a library of carbapenem-linker-fluorophore represented by Chemical Formula 1 of the present disclosure with the substrate of carbapenemase, and have completed the present disclosure.

DISCLOSURE

Technical Problem

The present disclosure is directed to providing a compound represented by Chemical Formula 1, which is capable of detecting a broad spectrum of carbapenem-resistant bacteria with high sensitivity.

The present disclosure is also directed to providing a probe for detecting antibiotic-resistant bacteria, which includes the compound.

The present disclosure is also directed to providing a reagent composition for detecting antibiotic-resistant bacteria, which contains the compound.

The present disclosure is also directed to providing a kit for diagnosing infection by antibiotic-resistant bacteria, which includes the compound.

The present disclosure is also directed to providing a method for detecting antibiotic-resistant bacteria using the compound.

Technical Solution

The present disclosure provides compound represented by Chemical Formula 1.

[Chemical Formula 1]

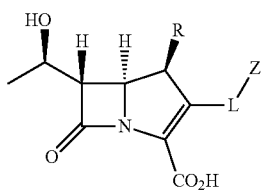

In an exemplary embodiment of the present disclosure, in Chemical Formula 1, R may be a hydrogen atom or $C_1$-$C_2$ alkyl.

In another exemplary embodiment of the present disclosure, in Chemical Formula 1, L serves as a linker connecting the carbapenem structure with a fluorescent dye, and may be substituted or unsubstituted vinyl, substituted or unsubstituted aryl, substituted or unsubstituted carbamate, substituted or unsubstituted thiocarbamate, substituted or unsubstituted amine, or substituted or unsubstituted pyridinium, more specifically any one selected from a group consisting of —(CH═CH)$_n$CH$_2$—, —(C≡C)$_n$CH$_2$—, —(CH═CH)$_n$CH$_2$—O—Ar—CH$_2$—, —(C≡C)$_n$CH$_2$—O—Ar—CH$_2$—, —(CH═CH)$_n$CH$_2$—S—Ar—CH$_2$—, —(C≡C)$_n$CH$_2$—S—Ar—CH$_2$—, —(CH═CH)$_n$CH$_2$—NH—Ar—CH$_2$—, —(C≡C)$_n$CH$_2$—NH—Ar—CH$_2$—, —(CH═CH)$_n$CH$_2$—OCON—, —(C≡C)$_n$CH$_2$—OCON—, —(CH═CH)$_n$CH$_2$—OCSN—,

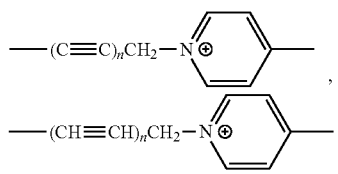

and —(C≡C)$_n$CH$_2$—OCSN—, wherein n may be 0, 1, 2, 3 or 4, Ar may be one or more selected from a group consisting of

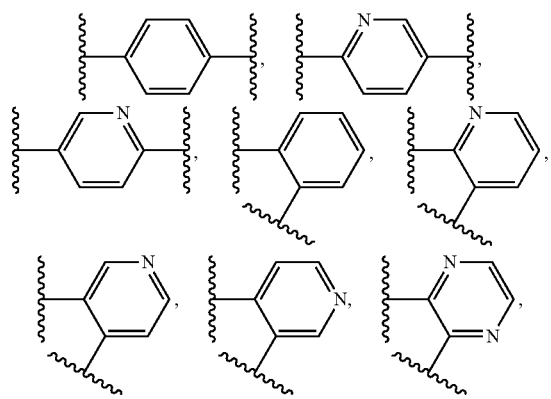

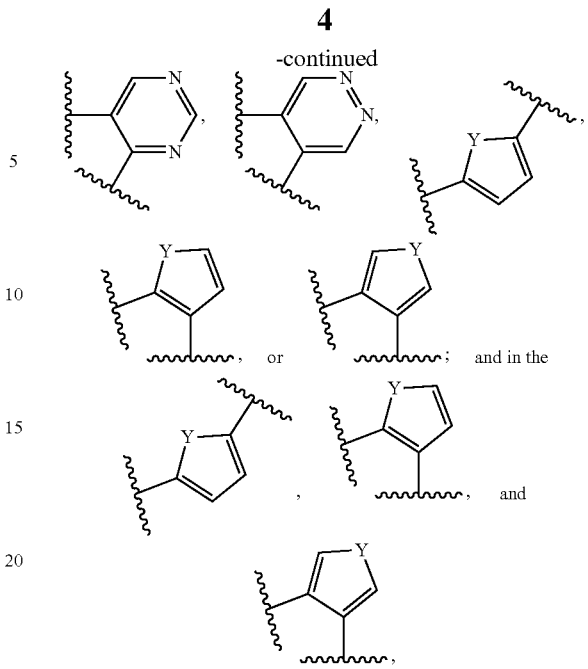

Y may be one or more selected from a group consisting of O, NH and S.

In another exemplary embodiment of the present disclosure, the fluorescent dye may be any one selected from a group consisting of coumarin, umbelliferone, aminocoumarin, fluorescein, resorufin, carboxyrhodamine, rhodamine, naphthalimide, cyanine, luciferin, CR110, EvoBlue, Alexa Fluor, Flamma, Indocyanine green, 2-((E)-2-((E)-2-(4-(2-carboxyethyl) phenoxy)-3-((E)-2-(3,3-dimethyl5-sulfonato-1-(3-(tri-methylammonio)-propyl) indolin-2-ylidene)ethylidene) cyclohex-1-enyl) vinyl)-3,3-dimethyl-1-(3-(trimethylammonio)-propyl)-3H-indolium-5-sulfonate disodium bromide and BODIPY.

In another exemplary embodiment of the present disclosure, the EvoBlue may be EvoBlue 10 or EvoBlue 30.

In another exemplary embodiment of the present disclosure, the Alexa Fluor may be one selected from a group consisting of Alexa Fluor 350, Alexa Fluor 405, Alexa Fluor 430, Alexa Fluor 488, Alexa Fluor 532, Alexa Fluor 546, Alexa Fluor 555, Alexa Fluor 568, Alexa Fluor 594, Alexa Fluor 633, Alexa Fluor 680, Alexa Fluor 700, Alexa Fluor 750 and Alexa Fluor 790.

In another exemplary embodiment of the present disclosure, the Flamma may be one selected from a group consisting of Flamma 496, Flamma 507, Flamma 530, Flamma 552, Flamma 560, Flamma 575, Flamma 581, Flamma 648, Flamma 675, Flamma 749, Flamma 774 and Flamma 775.

In another exemplary embodiment of the present disclosure, the BODIPY may be one selected from a group consisting of pyridyl BODIPY, BODIPY FL, BODIPY R6G, BODIPY TMR, BODIPY 581/591, BODIPY TR, BODIPY 630/650, BODIPY 650/665, BODIPY 558/568, BODIPY 564/570 and a combination thereof.

In another exemplary embodiment of the present disclosure, fluorescence may be emitted as the Z (fluorescent dye) and the L (linker) of Chemical Formula 1 are cleaved from the carbapenem structure (β-lactam ring) by β-lactamase or carbapenemase.

In another exemplary embodiment of the present disclosure, the compound represented by Chemical Formula 1 may be any compound selected from a group consisting of the following compounds:

[Compound OMCL01202]

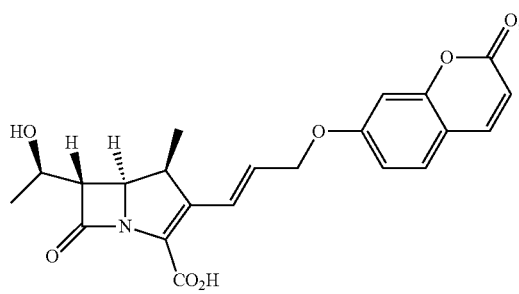

[Compound OMCL01203]

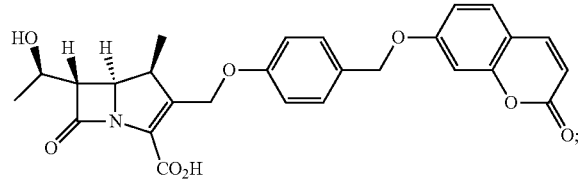

[Compound OMCL01204]

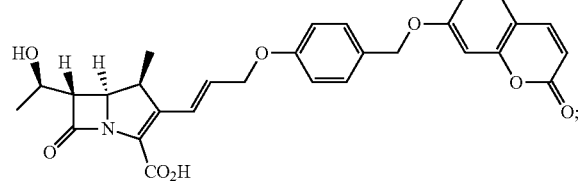

[Compound OMCL01205]

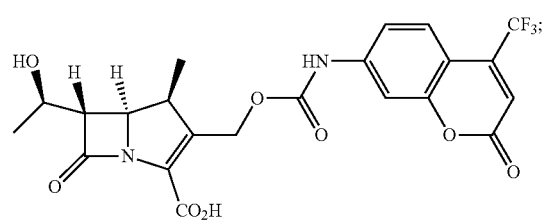

[Compound OMCL01206]

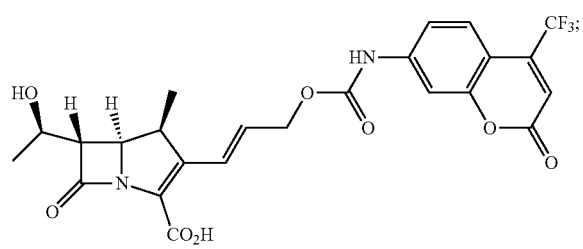

[Compound OMCL01207]

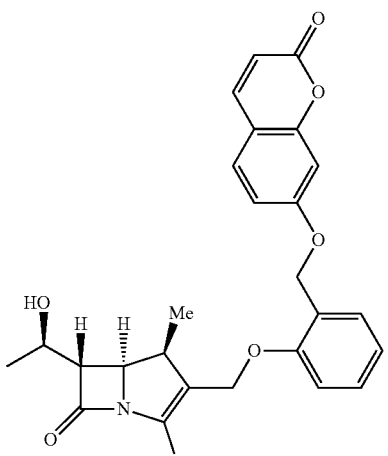

[Compound OMCL01208]

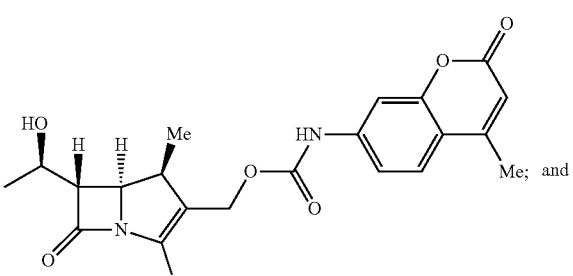

[Compound OMCL01209]

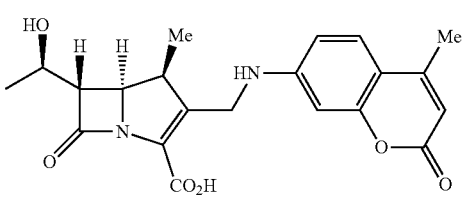

wherein TBS is t-butyldimethylsilyl and PNB is p-nitrobenzyl.

The present disclosure also provides a probe for detecting antibiotic-resistant bacteria, which includes the compound.

The present disclosure also provides a reagent composition for detecting antibiotic-resistant bacteria, which contains the compound.

The present disclosure also provides a kit for diagnosing infection by antibiotic-resistant bacteria, which includes the compound.

In an exemplary embodiment of the present disclosure, the antibiotic-resistant bacteria may have resistance to a carbapenem-based antibiotic, and the resistance may result from the ability of the bacteria to express β-lactamase or carbapenemase.

In another exemplary embodiment of the present disclosure, the carbapenem-based antibiotic may be any one having a β-lactam ring structure without limitation. Specifically, it may be one or more antibiotic selected from a group consisting of imipenem, meropenem, ertapenem and doripenem.

The present disclosure also provides a method for detecting antibiotic-resistant bacteria, which includes:
(a) a step of contacting the compound with a target sample; and (b) a step of detecting the intensity of fluorescence from the sample.

In an exemplary embodiment of the present disclosure, the method aims at detecting the presence of bacteria having resistance to a carbapenem-based antibiotic from among antibiotics, and the sample may be a biological sample from a patient suspected of infection by carbapenem-resistant bacteria. The biological sample may be one or more selected from a group consisting of a cell, a cell culture, blood, saliva, sputum, cerebrospinal fluid, urine, feces and a combination thereof.

In another exemplary embodiment of the present disclosure, the patient suspected of infection by carbapenem-resistant bacteria may be a patient diagnosed with one or more disease selected from a group consisting of skin and soft tissue infection, febrile neutropenia, respiratory tract infection, upper respiratory tract infection, bronchiolitis, (pathogenic) pneumonia, sepsis, encephalomeningitis, surgical infection, dysentery, infectious sinusitis, peritonitis, anthrax, Lyme disease, osteomyelitis, legionellosis, brucellosis, acute enteritis, community-acquired respiratory tract infection, trachoma, neonatal inclusion conjunctivitis, botulinum food poisoning, acute food poisoning, diarrhea, hemorrhagic colitis, bronchitis, gastric ulcer, endocarditis, *salmonellosis*, gastroenteritis, opportunistic infection, otitis media, paranasal sinusitis, pharyngitis, acne, keratosis pilaris, rosacea, harlequin ichthyosis, xeroderma pigmentosum, keratoderma, eczema and necrotizing fasciitis, or a patient suspected of the disease.

The present disclosure also provides a method for preparing a compound of Chemical Formula 1, which includes:
i) a step of preparing a compound represented by Chemical Formula 3 from a compound represented by Chemical Formula 2;
ii) a step of preparing a compound represented by Chemical Formula 4 by mixing the compound represented by Chemical Formula 3 with a fluorescent dye;
iii) a step of obtaining a compound represented by Chemical Formula 5 by dissolving the compound represented by Chemical Formula 4 in a mixture solution of N-methyl-2-pyrrolidinone and dimethylformamide, adding ammonium hydrogen fluoride, stirring at room temperature, and then terminating reaction with an aqueous sodium bicarbonate solution; and
iv) a step of dissolving the compound represented by Chemical Formula 5 in an aqueous tetrahydrofuran solution, stirring and filtering the mixture, and then obtaining the compound represented by Chemical Formula 1:

[Chemical Formula 1]
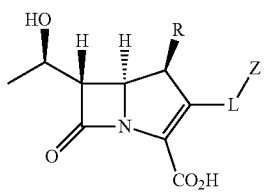

[Chemical Formula 2]
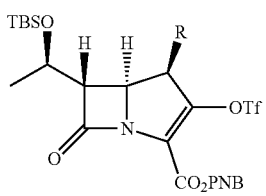

[Chemical Formula 3]
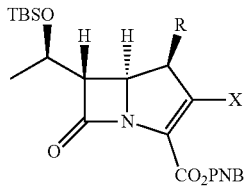

[Chemical Formula 4]
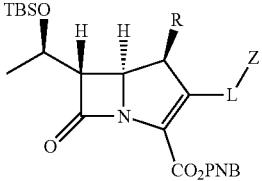

[Chemical Formula 5]
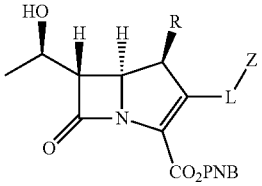

wherein
X is —(CH=CH)$_n$CH$_2$OH(n=0-4) or propargyl alcohol,
TBS is t-butyldimethylsilyl and PNB is p-nitrobenzyl, and
R, L and Z are the same as described above.

In the step i), the compound represented by Chemical Formula 2 may be Compound 2, and the compound represented by Chemical Formula 3 may be Compound 6 prepared by reacting Compound 2 with Compound 3; or Compound 7 prepared by reacting Compound 2 with Compound 5:

[Compound 2]
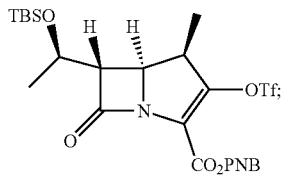

[Compound 3]

[Compound 5]
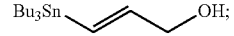

[Compound 6]
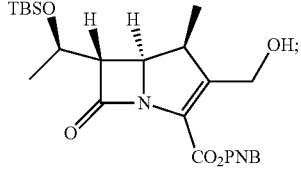

[Compound 7]
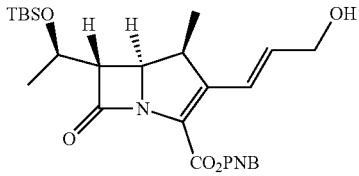

wherein TBS is t-butyldimethylsilyl and PNB is p-nitrobenzyl.

The preparation method is described in more detail in the Examples section.

Advantageous Effects

Since a compound according to the present disclosure and a probe including the compound can detect carbapenemase and β-lactamase with high sensitivity, they are applicable to various biochemical researches. In addition, since they allow clinical detection of antibiotic-resistant bacteria, which is not possible with the existing phenotyping assay method, and molecular diagnosis of antibiotic-resistant bacterial infectious diseases and analysis of antibiotic-resistant bacteria from a target sample with high sensitivity, they can be effectively applied to medicinal uses such as in-vitro diagnosis (including clinical and microbiological diagnosis and on-site diagnosis).

BEST MODE

In the present disclosure, it was confirmed that a broad spectrum of carbapenem-resistant bacteria can be detected with high sensitivity by contacting a library of carbapenem-linker-fluorophore represented by Chemical Formula 1 with a substrate of carbapenemase.

Accordingly, in an aspect, the present disclosure relates to a compound represented by Chemical Formula 1.

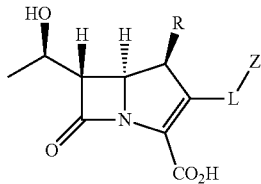

[Chemical Formula 1]

In the above formula,

R is a hydrogen atom or $C_1$-$C_2$ alkyl;

L is substituted or unsubstituted vinyl; substituted or unsubstituted aryl; substituted or unsubstituted carbamate; or substituted or unsubstituted thiocarbamate; substituted or unsubstituted amine; substituted or unsubstituted pyridinium; and Z is a fluorescent dye.

In the present disclosure, the L may be any one selected from a group consisting of —(CH=CH)$_n$CH$_2$—, —(C≡C)$_n$CH$_2$—, —(CH=CH)$_n$CH$_2$—O—Ar—CH$_2$—, —(C≡C)$_n$CH$_2$—O—Ar—CH$_2$—, —(CH=CH)$_n$CH$_2$—S—Ar—CH$_2$—, —(C≡C)$_n$CH$_2$—S—Ar—CH$_2$—, —(CH=CH)$_n$CH$_2$—NH—Ar—CH$_2$—, —(C≡C)$_n$CH$_2$—NH—Ar—CH$_2$—, —(CH=CH)$_n$CH$_2$—OCON—, —(C≡C)$_n$CH$_2$—OCON—, (CH=CH)$_n$CH$_2$—OCSN—,

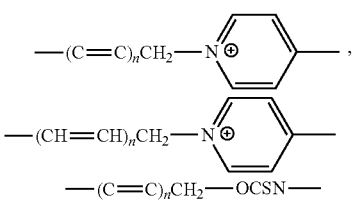

and

—(C≡C)$_n$CH$_2$—OCSN—

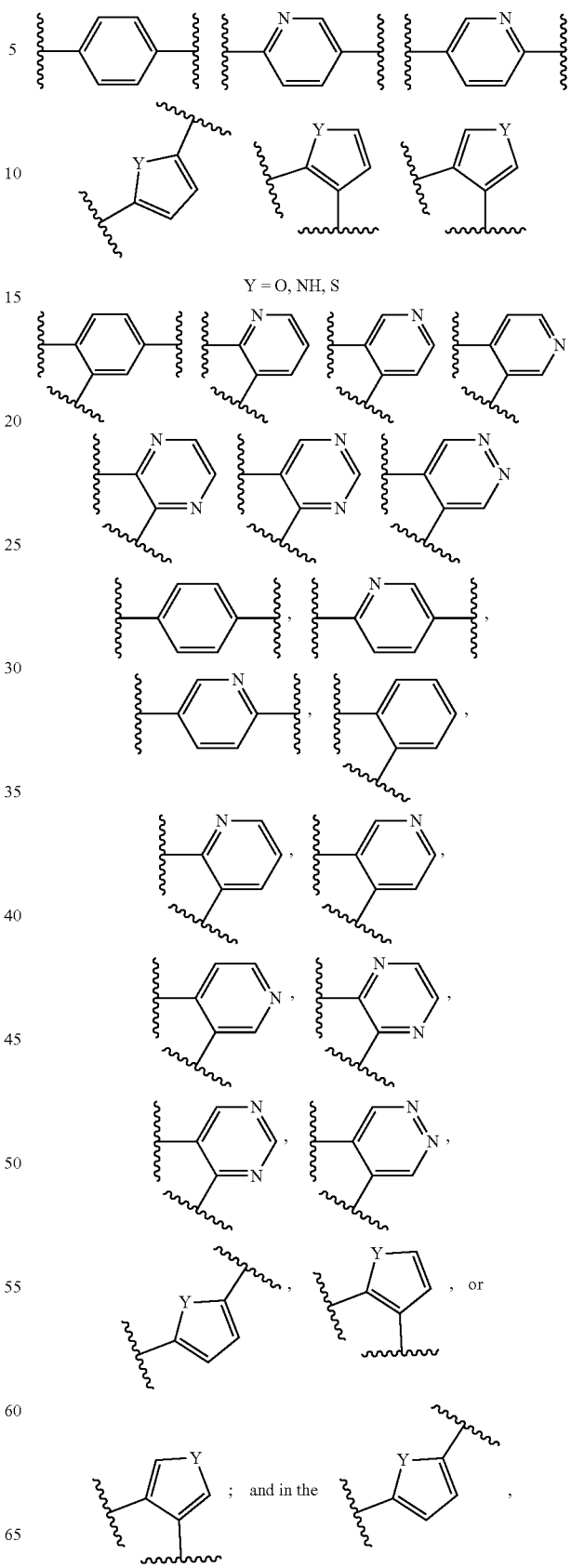

(Ar =

Y = O, NH, S

; and in the

, or

,

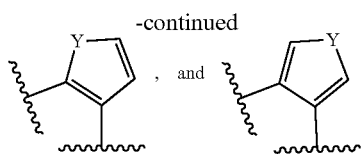

Y is O, NH or S, n=0-4).

In the present disclosure, the L is a linker which connects the core structure of Chemical Formula 1 with Z.

In the present disclosure, the fluorescent dye may be any one selected from a group consisting of coumarin, umbelliferone, aminocoumarin, fluorescein, resorufin, carboxyrhodamine, rhodamine, naphthalimide, cyanine, luciferin, CR110, EvoBlue, Alexa Fluor, Flamma, Indocyanine green, 2-((E)-2-((E)-2-(4-(2-carboxyethyl) phenoxy)-3-((E)-2-(3,3-dimethyl5-sulfonato-1-(3-(tri-methylamino)-propyl) indolin-2-ylidene)ethylidene) cyclohex-1-enyl) vinyl)-3,3-dimethyl-1-(3-(trimethylamino)-propyl)-3H-indolium-5-sulfonate disodium bromide and BODIPY. However, the fluorescent dye is not limited as long as it emits light in the fluorescence region when it is cleaved from the β-lactam ring structure.

In the present disclosure, the EvoBlue may be EvoBlue 10 or EvoBlue 30, the Alexa Fluor may be one selected from a group consisting of Alexa Fluor 350, Alexa Fluor 405, Alexa Fluor 430, Alexa Fluor 488, Alexa Fluor 532, Alexa Fluor 546, Alexa Fluor 555, Alexa Fluor 568, Alexa Fluor 594, Alexa Fluor 633, Alexa Fluor 680, Alexa Fluor 700, Alexa Fluor 750 and Alexa Fluor 790, and the Flamma may be one selected from a group consisting of Flamma496, Flamma507, Flamma 530, Flamma 552, Flamma 560, Flamma 575, Flamma 581, Flamma 648, Flamma 675, Flamma 749, Flamma 774 and Flamma 775.

In addition, in the present disclosure, the BODIPY may be any one selected from a group consisting of pyridyl BODIPY, BODIPY FL, BODIPY R6G, BODIPY TMR, BODIPY 581/591, BODIPY TR, BODIPY 630/650, BODIPY 650/665, BODIPY 558/568, BODIPY 564/570 and a combination thereof.

In the present disclosure, the "fluorescent dye" refers to a fluorescent moiety, and the fluorescent moiety may mean a fluorescent molecule which absorbs light of a specific frequency (e.g., UV light) and generates a fluorescence signal when cleaved from Chemical Formula 1, a derivative thereof or a conjugate thereof. For example, the fluorescent moiety may be a quencher dye. Non-limiting examples of the fluorescent moiety may include phenolic dyes such as umbelliferone, fluorescein and resorufin; aromatic amines; other compounds such as rhodamine, etc. In addition, the fluorescent moiety may be, for example, coumarin and related dyes; xanthene dyes such as fluorescein, rhodol and rhodamine; resorufin; cyanine dyes; bimane dyes; acridines; isoindole; dansyl dyes; aminophthalic hydrazides such as luminol and isoluminol derivatives; aminophthalimide; aminonaphthalimide; aminobenzofuran; aminoquinoline; dicyanohydroquinone; BODIPY; or europium and terbium complexes and related compounds.

In addition, the fluorescent moiety may further include a free carboxyl group, an ester (e.g., N-hydroxysuccinimide (NHS) ester) or a maleimide derivative, and may also include a streptavidin, biotin, phalloidin, amine, azide or iodoacetamide conjugate.

In the present disclosure, the fluorescent moiety may be bound to the carbapenem-based compound via the linker. Accordingly, the fluorescent moiety according to a specific exemplary embodiment may exhibit fluorescence as it is cleaved from Chemical Formula 1 together with the linker (L) by β-lactamase or carbapenemase.

In the present disclosure, fluorescence may be emitted as Z is cleaved from Chemical Formula 1 together with L by β-lactamase or carbapenemase.

In an exemplary embodiment of the present disclosure, a broad spectrum of carbapenem-resistant bacteria can be detected using a substrate of carbapenemase using a library of the carbapenem-linker (red rectangle)-fluorophore.

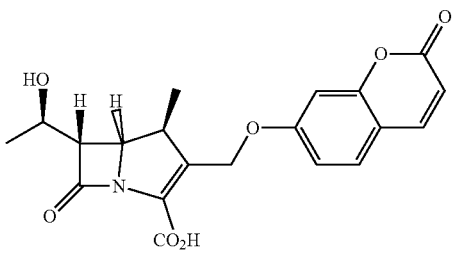

(CP-methylene-coumarin)

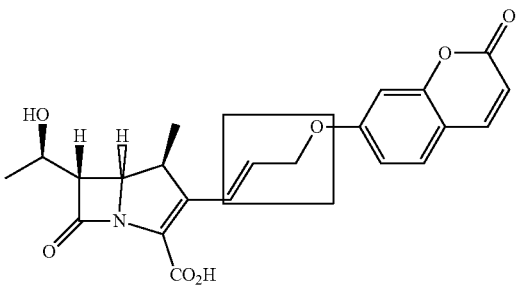

(CP-allyl-coumarin)

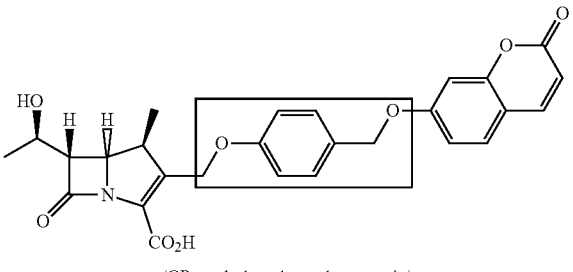

(CP-methylene-benzyl-coumarin)

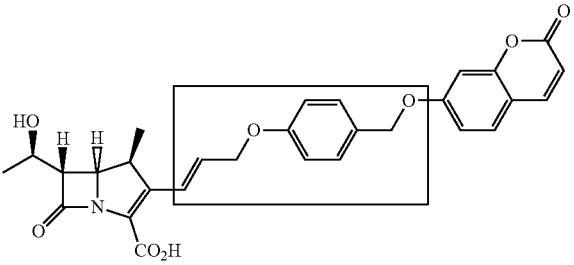

OMCL01205
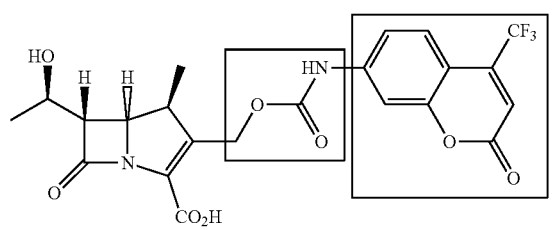
OMCL01206
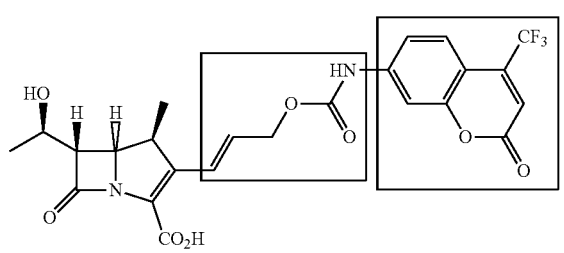
OMCL01207
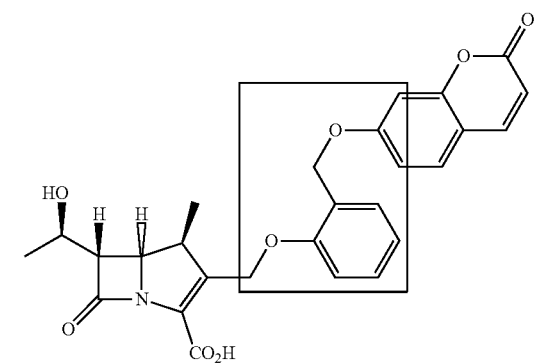
(CP-methylene-o-benzyl-coumarin)
OMCL01208
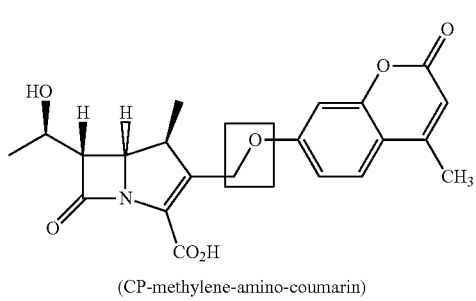
(CP-methylene-amino-coumarin)
OMCL01209
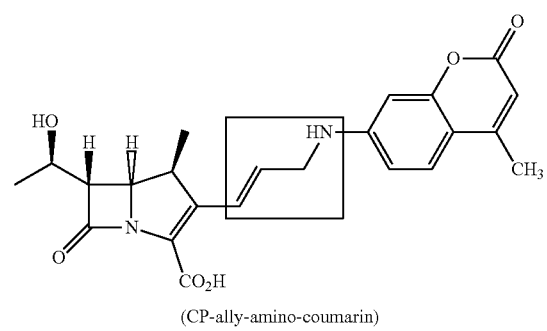
(CP-ally-amino-coumarin)
OMCL01201 = CPC-1
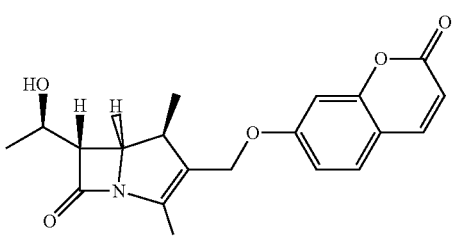
(CP-methylene-coumarin)
OMCL01202
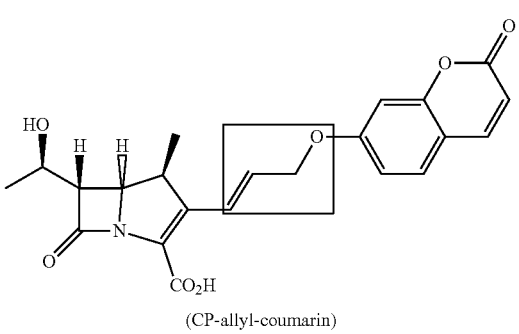
(CP-allyl-coumarin)
OMCL01203
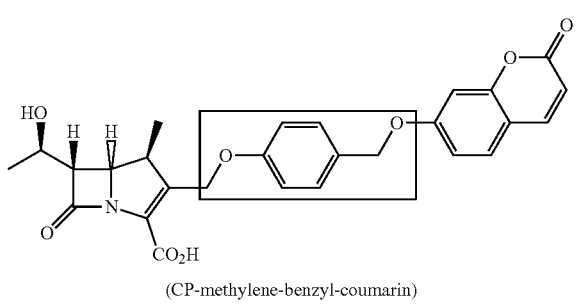
(CP-methylene-benzyl-coumarin)
OMCL01204
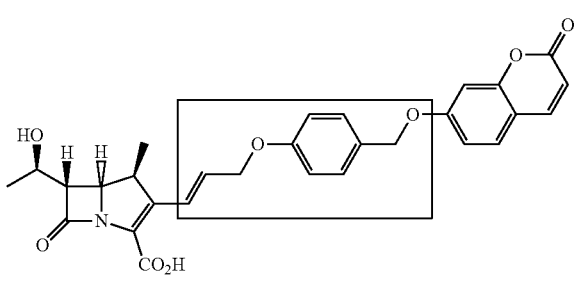
(CP-allyl-benzyl-coumarin)
OMCL01205
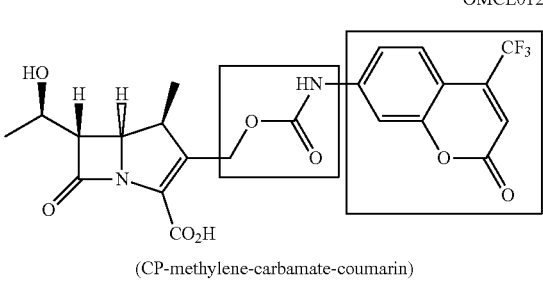
(CP-methylene-carbamate-coumarin)

-continued

OMCL01206

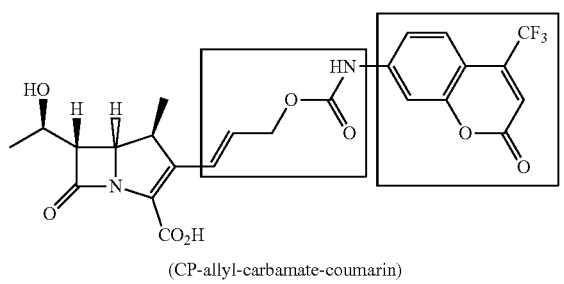
(CP-allyl-carbamate-coumarin)

OMCL01207

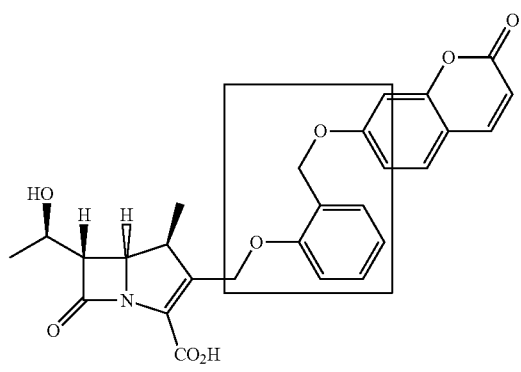
(CP-methylene-o-benzyl-coumarin)

OMCL01208

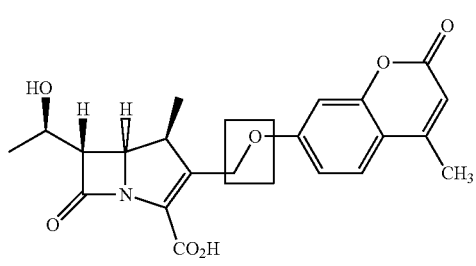
(CP-methylene-amino-coumarin)

OMCL01209

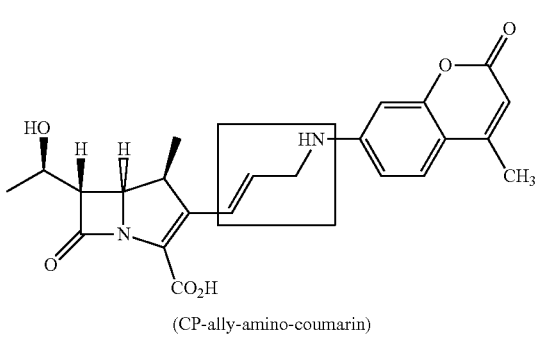
(CP-ally-amino-coumarin)

In another aspect, the present disclosure relates to a probe for detecting antibiotic-resistant bacteria, which includes the compound.

In the present disclosure, the antibiotic may be a carbapenem-based antibiotic, and the antibiotic-resistant bacteria may be carbapenemase-expressing bacteria.

In the present disclosure, the carbapenem-based antibiotic may be selected from a group consisting of imipenem, meropenem, ertapenem and doripenem, although not being limited thereto.

The following chemical formulas show the chemical structures of imipenem, meropenem, doripenem and ertapenem.

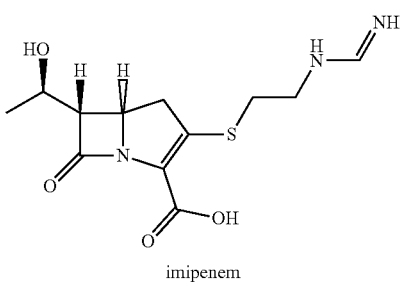
imipenem

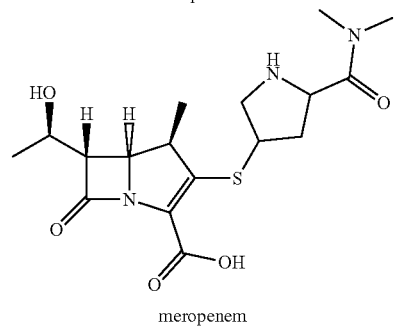
meropenem

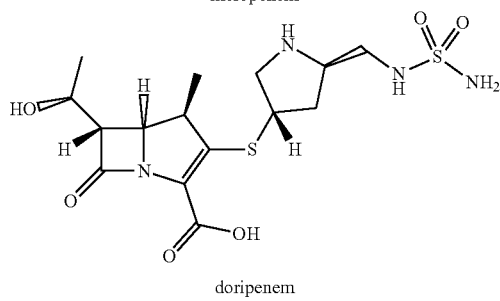
doripenem

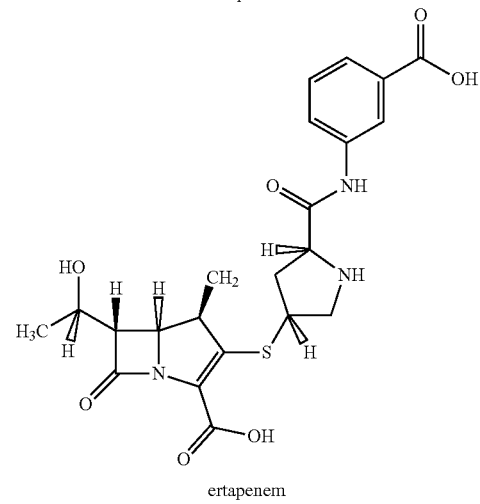
ertapenem

In another aspect, the present disclosure relates to a reagent composition for detecting antibiotic-resistant bacteria, which contains the compound.

In another aspect, the present disclosure relates to a kit for diagnosing infection by antibiotic-resistant bacteria, which includes the compound.

The fluorescence emitted from the compound represented by Chemical Formula 1 may be an indicator of the presence of ESBL, particularly carbapenemase and/or bacteria expressing the same, in a sample, and may be used for diagnosis of infectious diseases caused by the bacteria.

In the present disclosure, the bacterial infection may be infection by carbapenemase-expressing bacteria.

In the present disclosure, a disease caused by infection by carbapenemase-expressing bacteria may be one or more selected from a group consisting of skin and soft tissue infection, febrile neutropenia, respiratory tract infection, upper respiratory tract infection, bronchiolitis, (pathogenic) pneumonia, sepsis, encephalomeningitis, surgical infection, dysentery, infectious sinusitis, peritonitis, anthrax, Lyme disease, osteomyelitis, legionellosis, brucellosis, acute enteritis, community-acquired respiratory tract infection, trachoma, neonatal inclusion conjunctivitis, botulinum food poisoning, acute food poisoning, diarrhea, hemorrhagic colitis, bronchitis, gastric ulcer, endocarditis, *salmonellosis*, gastroenteritis, opportunistic infection, otitis media, paranasal sinusitis, pharyngitis, acne, keratosis pilaris, rosacea, harlequin ichthyosis, xeroderma pigmentosum, keratoderma, eczema and necrotizing fasciitis.

In the present disclosure, the "infectious disease" may refer to a disease or condition associated with the presence of an organism (infectious agent) in a subject or a patient. Particularly, it may refer to a "bacterial infectious disease". For example, a "carbapenem-based antibiotic-resistant bacterial infectious disease" may mean an antibiotic-resistant bacterial infectious disease which is not effectively treated with carbapenem-based antibiotics.

In the present disclosure, "diagnosis" may include decision of the susceptibility of a subject to a specific disease or disorder, decision of the presence of a specific disease or disorder in a subject, decision of the prognosis of a subject having a specific disease or disorder (e.g., identification of an infectious disease or status or decision of the responsiveness to or effect of the treatment of the disease) or therametrics (e.g., monitoring of the status of a subject in order to provide information about therapeutic effects). The subject is not limited as long as it is a mammal suspected of a bacterial infectious disease. Specifically, it may be human.

In another aspect, the present disclosure relates to a method for detecting antibiotic-resistant bacteria, which includes: (a) a step of contacting the compound with a target sample; and (b) a step of detecting the intensity of fluorescence from the sample.

In the present disclosure, the sample may be one or more selected from a group consisting of a cell culture, blood, saliva, sputum, cerebrospinal fluid, urine feces and a combination thereof.

The step of contacting may include a step of adding the biological sample or a target sample, which has been pretreated, to a composition containing the compound of Chemical Formula 1. The pretreatment of the sample may be performed adequately by those skilled in the art depending on purposes.

An infectious disease caused by antibiotic-resistant bacteria may be diagnosed or antibiotic-resistant bacteria may be detected by contacting (reacting) with the target sample and measuring fluorescence emission due to hydrolysis of the compound of Chemical Formula 1 and, finally, analyzing the intensity of the fluorescence. The analysis of the fluorescence signal may be performed using various methods known in the art, and the result is interpreted and processed using an adequate apparatus available in the art. For example, protocols and processes known in the art, including a fluorescence analyzer, a microplate reader, an automated processing system using robotic devices, a laser scanning system, etc., may be used.

Hereinafter, the present disclosure will be described in more detail through examples. The following examples are provided only to illustrate the present disclosure, and it will be obvious to those having ordinary skill in the art that the scope of the present disclosure is not limited by the examples.

MODE FOR INVENTION

Example 1: Preparation of Probe for Detecting Antibiotic-Resistant Bacteria 1.1. Preparation of 4-nitrobenzyl (R)-4-((2R,3S)-3-((R)-1-((tert-butyldimethylsilyl)oxy)ethyl)-4-oxoazetidin-2-yl)-2-diazo-3-oxopentanoate (1)

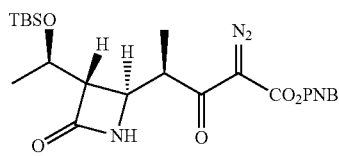

[Compound 1]

After dissolving 1-hydroxyethyl azetidin-2-one (5.00 g, 10.8 mmol) in anhydrous dimethylformamide (42.0 mL) under nitrogen gas, imidazole (4.42 g, 64.8 mmol) and tert-butyldimethylsilyl chloride (7.72 g, 51.2 mmol) were added at 0° C. The reaction mixture was stirred at room temperature for 12 hours. After terminating reaction by adding an aqueous ammonium chloride solution, the reaction mixture was extracted with ethyl acetate and distilled water. The organic layer was dried by adding anhydrous MgSO$_4$ and then filtered, and the filtrate was concentrated in vacuo. Compound 1 (6.16 g, 95%) was produced as white powder by purifying the resulting mixture on silica gel by column chromatography (ethyl acetate/n-hexane, 1:2 (v/V)).

$^1$H-NMR (400 MHZ, CDCl$_3$) δ 8.26 (d, J=8.6 Hz, 2H), 7.54 (d, J=8.6 Hz, 2H), 5.89 (s, 1H), 5.37 (d, J=13.2 Hz, 1H), 5.33 (d, J=13.2 Hz, 1H), 4.21-4.16 (m, 1H), 3.90-3.89 (m, 2H), 2.96 (d, J=2.9 Hz, 1H), 1.19 (d, J=6.0 Hz, 3H), 1.17 (d, J=5.9 Hz, 3H), 0.85 (s, 9H), 0.06 (s, 3H), 0.04 (s, 3H).

1.2. Preparation of 4-nitrobenzyl (4R,5R,6S)-6-((R)-1-((tert-butyldimethylsilyl)oxy)ethyl)-4-methyl-7-oxo-3-(((trifluoromethyl) sulfonyl)oxy)-1-azabicyclo[3.2.0]heptane-2-carboxylate (2)

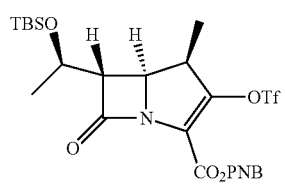

[Compound 2]

After dissolving diazomethane (100 mg, 0.198 mmol) in dichloromethane (0.600 mL) in a sealed tube, rhodium acetate dimer (1 mg, 0.002 mmol) and zinc chloride (1 mg, 0.006 mmol) were added. The reaction mixture was warmed to 60° C. and then stirred for 1 hour. After slowly cooling a mixture of the ketone intermediate to −78° C., 2,2,6,6-tetramethylpiperidine (40 μL, 0.238 mmol) and N,N-diisopropylethylamine (17 μL, 0.100 mmol) were added and trifluoromethanesulfonic anhydride (37 μL, 1.68 mmol) was added dropwise over 5 minutes. After stirring for 1 hour, Compound 2 (117 mg, 97%) was produced as white powder by warming the mixture to room temperature and purifying on silica gel by column chromatography (dichloromethane).

$^1$H-NMR (400 MHZ, CDCl$_3$) δ 8.22 (d, J=8.7 Hz, 2H), 7.62 (d, J=8.8 Hz, 2H), 5.42 (d, J=13.6 Hz, 1H), 5.35 (d, J=13.6 Hz, 1H), 4.34 (dd, J=3.4, 11.0 Hz, 1H), 4.30-4.26 (m, 1H), 3.41-3.29 (m, 2H), 1.29 (d, J=7.3 Hz, 3H), 1.22 (d, J=6.2 Hz, 3H), 0.87 (s, 9H), 0.08 (s, 3H), 0.06 (s, 3H).

<Ketone Intermediate>

$^1$H-NMR (400 MHZ, CDCl$_3$) δ 8.23 (d, J=8.6 Hz, 2H), 7.52 (d, J=8.5 Hz, 2H), 5.31 (d, J=13.3 Hz, 1H), 5.25 (d, J=13.4 Hz, 1H), 4.71 (s, 1H), 4.32-4.28 (m, 1H), 4.24 (dd, J=2.4, 7.9 Hz, 1H), 3.22 (dd, J=2.4, 5.4 Hz, 1H), 2.82-2.74 (m, 1H), 1.26 (d, J=6.2 Hz, 3H), 1.20 (d, J=7.8 Hz, 3H), 0.87 (s, 9H), 0.09 (s, 3H), 0.07 (s, 3H).

1.3 Preparation of. (tributylstannyl) methanol (3)

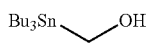

[Compound 3]

After dissolving diisopropylamine (2.9 mL, 20.6 mmol) in anhydrous tetrahydrofuran (86 mL), n-butyllithium (1.6 M in hexane, 12.9 mL, 20.6 mmol) was added slowly at −78° C. After conducting reaction for 5 minutes, tributyltin hydride (5 g, 17.2 mmol) was added dropwise over 30 minutes. After stirring the mixture for 20 minutes, adding paraformaldehyde (722 mg, 24.1 mmol) and warming to room temperature, the mixture was stirred for 12 hours. After terminating reaction using an aqueous ammonium chloride solution, the reaction mixture was extracted with diethyl ether and an aqueous solution. The organic layer was dried by adding anhydrous MgSO$_4$ and then filtered, and the filtrate was concentrated in vacuo. Compound 3 (3.05 g, 55%) was produced as colorless oil by purifying the resulting mixture on silica gel by column chromatography (diethyl ether/n-hexane, 1:3 (v/v)). $^1$H-NMR (400 MHZ, CDCl$_3$) δ 4.01 (d, J=6.6 Hz, 1H), 4.00 (d, J=6.6 Hz, 1H), 1.55-1.47 (m, 6H), 1.35-1.25 (m, 6H), 0.93-0.67 (m, 15H).

1.4. Preparation of tert-butyldimethyl (prop-2-yn-1-yloxy) silane (4)

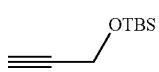

[Compound 4]

After dissolving propargyl alcohol (1.00 g, 17.8 mmol) in dichloromethane (42.0 mL), imidazole (1.82 g, 26.8 mmol) and tert-butyldimethylsilyl chloride (4.03 g, 26.8 mmol) were added at 0° C. The reaction mixture was warmed to room temperature and stirred for 12 hours. After terminating reaction using an aqueous ammonium chloride solution, the reaction mixture was extracted with diethyl ether and an aqueous solution. The organic layer was dried using anhydrous MgSO$_4$ and then filtered, and the filtrate was concentrated in vacuo. Compound 4 (2.10 g, 69%) was produced as colorless oil by purifying the resulting mixture on silica gel by column chromatography (diethyl ether/n-hexane, 1:30 (v/v)).

$^1$H-NMR (400 MHZ, CDCl$_3$) δ 4.30 (d, J=2.4 Hz, 2H), 2.38 (d, J=2.4 Hz, 1H), 0.90 (s, 9H), 0.12 (s, 6H).

1.5. Preparation of (E)-3-(tributylstannyl) prop-2-en-1-ol (5)

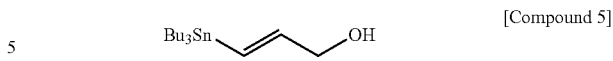

[Compound 5]

Azobisisobutyronitrile (289 mg, 1.76 mmol) and tributyltin hydride (1.9 mL, 7.05 mmol) were added to the silyl ether compound (Compound 4, 1.00 g, 5.87 mmol). The reaction mixture was warmed to 80° C. and then stirred for 2 hours. After cooling the reaction mixture to 0° C. and dissolving in anhydrous tetrahydrofuran (11.7 mL), 1.0 M tetrabutylammonium fluoride dissolved in tetrahydrofuran (11.7 mL, 11.7 mmol) was added and the mixture was stirred for 2 hours. After terminating reaction using an aqueous ammonium chloride solution, the reaction mixture was extracted with diethyl ether and an aqueous solution. The organic layer was dried using anhydrous MgSO$_4$ and then filtered, and the filtrate was concentrated in vacuo. Compound 5 (1.34 g, 66%) was produced as colorless oil by purifying the resulting mixture on silica gel by column chromatography (diethyl ether/n-hexane, 1:10 (v/V)).

$^1$H-NMR (400 MHZ, CDCl$_3$) δ 6.25-6.08 (m, 2H), 4.15 (bs, 2H), 1.50-1.44 (m, 6H), 1.32-1.26 (m, 6H), 0.90-0.85 (m, 15H).

1.6. Preparation of 4-nitrobenzyl (4S,5R,6S)-6-((R)-1-((tert-butyldimethylsilyl)oxy)ethyl)-3-(hydroxymethyl-4-methyl-7-oxo-1-azabicyclo[3.2.0]heptane-2-carboxylate (6)

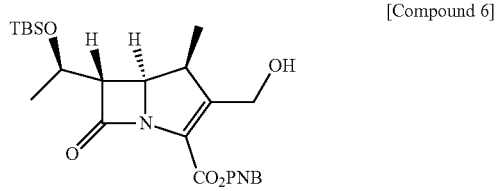

[Compound 6]

After dissolving tri (2-furyl)phosphine (11.4 mg, 0.049 mmol), tris (dibenzylideneacetone) dipalladium-chloroform adduct (25.4 mg, 0.025 mmol) and zinc chloride (22.4 mg, 0.164 mmol) in anhydrous hexamethylphosphoric triamide (0.5 mL), the triflate compound (Compound 2, 100 mg, 0.164 mmol) and the stannane compound (Compound 3, 211 mg, 0.656 mmol) dissolved in hexamethylphosphoric triamide (0.1 mL) were slowly added to the mixture at 70° C. After stirring for 2 hours and cooling to 5° C., reaction was terminated using an aqueous ammonium chloride solution. The reaction mixture was extracted using ethyl acetate and an aqueous solution. The organic layer was dried using anhydrous MgSO$_4$ and then filtered, and the filtrate was concentrated in vacuo. Compound 6 (42.0 mg, 52%) was produced as white powder by purifying the resulting mixture on silica gel by column chromatography (ethyl acetate/n-hexane, 1:8 to 1:2 (v/v)).

$^1$H-NMR (400 MHZ, CDCl$_3$) δ 8.22 (d, J=8.7 Hz, 2H), 7.66 (d, J=8.7 Hz, 2H), 5.46 (d, J=13.8 Hz, 1H), 5.27 (d, J=13.9 Hz, 1H), 4.54 (dd, J=6.5, 14.8 Hz, 1H), 4.39 (dd, J=5.6, 14.8 Hz, 1H), 4.27-4.22 (m, 2H), 3.28-3.22 (m, 1H), 3.08-3.05 (m, 1H), 1.24 (d, J=6.2 Hz, 3H), 1.21 (d, J=7.4 Hz, 3H), 0.86 (s, 9H), 0.08 (s, 3H), 0.06 (s, 3H).

1.7. Preparation of 4-nitrobenzyl (4S,5R,6S)-6-((R)-1-((tert-butyldimethylsilyl)oxy)ethyl)-3-((E)-3-hydroxyprop-1-en-1-yl)-4-methyl-7-oxo-1-azabicyclo[3.2.0]heptane-2-carboxylate (7)

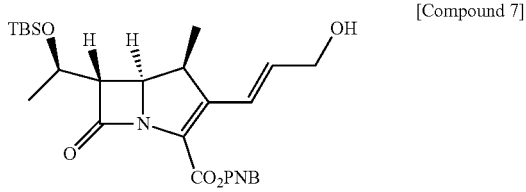

[Compound 7]

After dissolving tri (2-furyl)phosphine (19.1 mg, 0.082 mmol), tris (dibenzylideneacetone) dipalladium-chloroform adduct (42.5 mg, 0.041 mmol) and zinc chloride (10.9 mg, 0.182 mmol) in anhydrous N-methyl-2-pyrrolidinone (10.3 mL), the triflate compound (Compound 2, 500 mg, 0.821 mmol) and the stannane compound (Compound 5, 428 mg, 1.232 mmol) were added and the mixture was stirred at room temperature for 12 hours. After the stirring, the mixture was cooled to 5° C. and reaction was terminated using an aqueous ammonium chloride solution. The reaction mixture was extracted using ethyl acetate and an aqueous solution. The organic layer was dried using anhydrous $MgSO_4$ and then filtered, and the solvent was removed from the filtrate in vacuo. Compound 7 (315 mg, 74%) was produced as white powder by purifying the resulting mixture on silica gel by column chromatography (ethyl acetate/n-hexane, 1:4 to 1:2 (v/v)).

$^1$H-NMR (400 MHZ, $CDCl_3$) δ 8.22 (d, J=8.8 Hz, 2H), 7.67 (d, J=8.8 Hz, 2H), 7.31 (d, J=16.3 Hz, 1H), 6.20 (dt, J=5.5, 16.2 Hz, 1H), 5.44 (d, J=13.9 Hz, 1H), 5.27 (d, J=13.9 Hz, 1H), 5.27 (d, J=13.9 Hz, 1H), 4.32 (bs, 2H), 4.29-4.23 (m, 1H), 4.20 (dd, J=2.7, 9.4 Hz, 1H), 3.41-3.33 (m, 1H), 3.23 (dd, J=2.7, 5.6 Hz, 1H), 1.27 (d, J=6.2 Hz, 3H), 1.22 (d, J=7.3 Hz, 3H), 0.86 (s, 9H), 0.07 (s, 3H), 0.05 (s, 3H).

1.8. Preparation of 4-nitrobenzyl (4S,5R,6S)-6-((R)-1-((tert-butyldimethylsilyl)oxy)ethyl)-4-methyl-7-oxo-3-((E)-3-((2-oxo-2H-chromen-7-yl)oxy) prop-1-en-1-yl)-1-azabicyclo[3.2.0]hept-2-ene-2-carboxylate (8)

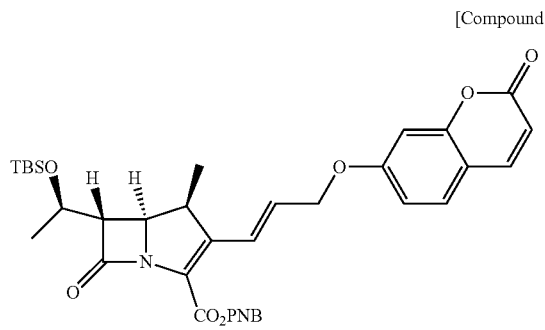

[Compound 8]

After dissolving the alcohol compound (Compound 7, 100 mg, 0.194 mmol) in toluene (3.9 mL), umbelliferone (34.6 mg, 0.213 mmol) and triphenylphosphine (68.0 mg, 0.233 mmol) were added at 0° C. After stirring for 2 minutes, diisopropyl azodicarboxylate (49 μL, 0.290 mmol) was added to the mixture. The reaction mixture was warmed to room temperature and then stirred for 30 minutes. After terminating reaction using an aqueous ammonium chloride solution, the reaction mixture was extracted with ethyl acetate and distilled water. The organic layer was dried using anhydrous $MgSO_4$ and then filtered, and the filtrate was concentrated in vacuo. Compound 8 (119 mg, 91%) was produced as white powder by purifying the resulting mixture on silica gel by column chromatography (ethyl acetate/n-hexane, 1:2 (v/v)).

$^1$H-NMR (400 MHZ, $CDCl_3$) δ 8.22 (d, J=8.6 Hz, 2H), 7.67 (d, J=8.7 Hz, 2H), 7.64 (d, J=9.6 Hz, 1H), 7.47 (d, J=8.3 Hz, 1H), 7.38 (d, J=8.6 Hz, 1H), 6.85 (dd, J=2.3, 8.6 Hz, 1H), 6.81 (d, J=7.0 Hz, 1H), 6.28-6.17 (m, 2H), 5.45 (d, J=13.8 Hz, 1H), 5.28 (d, J=14.0 Hz, 1H), 4.74 (d, J=5.8 Hz, 2H), 4.27-4.21 (m, 2H), 3.42-3.37 (m, 1H), 3.25 (dd, J=2.6, 5.4 Hz, 1H), 1.26 (d, J=6.2 Hz, 6H), 0.85 (s, 9H), 0.08 (s, 3H), 0.06 (s, 3H).

1.9. Preparation of 4-nitrobenzyl (4S,5R,6S)-6-((R)-1-hydroxyethyl)-4-methyl-7-oxo-3-((E)-3-((2-oxo-2H-chromen-7-yl)oxy) prop-1-en-1-yl)-1-azabicyclo[3.2.0]hept-2-ene-2-carboxylate (9)

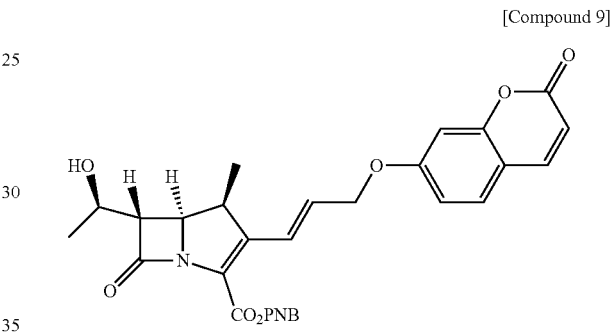

[Compound 9]

After dissolving the silyl ether compound (Compound 8, 40.1 mg, 0.059 mmol) in a 1:3 mixture of N-methyl-2-pyrrolidinone and dimethylformamide (1.2 mL), ammonium hydrogen fluoride (13.6 mg, 0.238 mmol) was added. The reaction mixture was stirred at room temperature for 30 hours. After terminating reaction with an aqueous sodium bicarbonate solution, the reaction mixture was extracted with ethyl acetate and distilled water. The organic layer was dried by adding anhydrous $MgSO_4$ and then filtered, and the filtrate was concentrated in vacuo. Compound 9 (24.0 mg, 75%) was produced as white powder by purifying the resulting mixture on silica gel by column chromatography (ethyl acetate/n-hexane, 3:1 (v/v)).

$^1$H-NMR (400 MHZ, $CDCl_3$) δ 8.21 (d, J=8.7 Hz, 2H), 7.66 (d, J=8.7 Hz, 2H), 7.63 (d, J=9.6 Hz, 1H), 7.45 (d, J=16.3 Hz, 1H), 7.37 (d, J=8.6 Hz, 1H), 6.83 (dd, J=2.4, 8.6 Hz, 1H), 6.80 (d, J=2.3 Hz, 1H), 6.28 (d, J=4.8 Hz, 1H), 6.20 (dt, J=5.7, 16.3 Hz, 1H), 5.49 (d, J=13.8 Hz, 1H), 5.25 (d, J=13.8 Hz, 1H), 4.73 (d, J=5.8 Hz, 2H), 4.26-4.23 (m, 2H), 3.47-3.43 (m, 1H), 3.28 (dd, J=2.6, 6.9 Hz, 1H), 1.37 (d, J=6.2 Hz, 3H), 1.25 (d, J=7.2 Hz, 3H).

1.10. Preparation of (4S,5R,6S)-6-((R)-1-hydroxyethyl)-4-methyl-7-oxo-3-((E)-3-((2-oxo-2H-chromen-7-yl)oxy)prop-1-en-1-yl)-1-azabicyclo[3.2.0]hept-2-ene-2-carboxylic acid (OMCL01202)

[Compound OMCL01202]

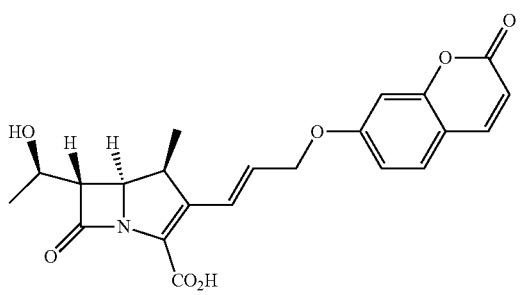

After dissolving Compound 9 (36.0 mg, 0.066 mmol) and 5% Rh/C (4.2 mg) in a 2:1 mixture of tetrahydrofuran and an aqueous solution (2.1 mL) at 0° C., the mixture was warmed to room temperature. After stirring for 2 hours under hydrogen gas, the reaction mixture was filtered using a PTFE syringe filter. Compound OMCL01202 (12.0 mg, 44%) was produced as white powder by purifying the filtrate by preparative RP-HPLC (acetonitrile/aqueous solution, 2:8 to 100:0 (v/v)) and freeze-drying under reduced pressure.

$^1$H-NMR (400 MHZ, CD$_3$OD) δ 7.87 (d, J=9.5 Hz, 1H), 7.52 (d, J=8.6 Hz, 1H), 7.46 (d, J=16.3 Hz, 1H), 6.97 (dd, J=2.4, 8.6 Hz, 1H), 6.93 (d, J=2.3 Hz, 1H), 6.22 (d, J=9.5 Hz, 1H), 6.03 (dt, J=6.1, 16.2 Hz, 1H), 4.74 (d, J=6.0 Hz, 2H), 4.10-4.05 (m, 2H), 3.37-3.26 (m, 1H), 3.15 (dd, J=2.4, 7.5 Hz, 1H), 1.28 (d, J=6.3 Hz, 3H), 1.27 (d, J=7.2 Hz, 3H).

1.11. Preparation of tert-butyl (4-((tert-butyldimethylsilyl)oxy)benzyl)oxy) dimethylsilane (11)

[Compound 11]

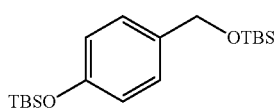

After dissolving hydroxybenzyl alcohol (500 mg, 4.03 mmol) in anhydrous dimethylformamide (20.2 mL), imidazole (2.02 g, 16.1 mmol) and tert-butyldimethylsilyl chloride (2.42 g, 16.1 mmol) were added at 0° C. The reaction mixture was warmed to room temperature and then stirred for 12 hours. After terminating reaction using an aqueous ammonium chloride solution, the reaction mixture was extracted with ethyl acetate and an aqueous solution. The organic layer was dried using anhydrous MgSO$_4$ and then filtered, and the filtrate was concentrated in vacuo. Compound 11 (1.40 g, 99%) was produced as colorless oil by purifying the resulting mixture on silica gel by column chromatography (ethyl acetate/n-hexane, 1:8 to 1:4 (v/V)).

$^1$H-NMR (400 MHZ, CDCl$_3$) δ 7.17 (d, J=8.4 Hz, 2H), 6.79 (d, J=8.5 Hz, 2H), 4.67 (s, 2H), 0.98 (s, 9H), 0.93 (s, 9H), 0.18 (s, 6H), 0.08 (s, 6H).

1.12. Preparation of (4-((tert-butyldimethylsilyl)oxy)phenyl) methanol (12)

[Compound 12]

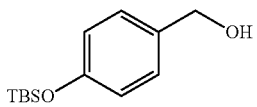

After dissolving the silyl ether compound (Compound 11, 35.3 mg, 0.10 mmol) in methanol (0.3 mL) at room temperature, N-iodosuccinimide (1.1 mg, 0.005 mmol) was added. After stirring for 12 hours and terminating reaction using an aqueous ammonium chloride solution, the reaction mixture was extracted with ethyl acetate and an aqueous solution. The organic layer was dried using anhydrous MgSO$_4$ and then filtered, and the filtrate was concentrated in vacuo. Compound 12 (21.0 mg, 88%) was produced as colorless oil by purifying the resulting mixture on silica gel by column chromatography (ethyl acetate/n-hexane, 1:4 (v/v)). $^1$H-NMR (400 MHZ, CDCl$_3$) δ 7.22 (d, J=8.5 Hz, 2H), 6.82 (dt, J=2.3, 9.0 Hz, 2H), 4.60 (s, 2H), 0.98 (s, 9H), 0.19 (s, 6H).

1.13. Preparation of 7-((4-((tert-butyldimethylsilyl)oxy)benzyl)oxy)-2H-chromen-2-one (13)

[Compound 13]

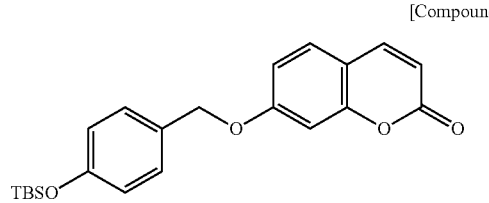

After dissolving the benzyl alcohol compound (Compound 12, 1.5 g, 5.34 mmol) in toluene (108 mL), umbelliferone (961 mg, 5.927 mmol) and triphenylphosphine (1.89 g, 6.47 mmol) were added at 0° C. After stirring for 2 minutes, diisopropyl azodicarboxylate (1.37 mL, 8.08 mmol) was added to the mixture. The reaction mixture was warmed to room temperature and then stirred for 30 minutes. After terminating reaction using an aqueous ammonium chloride solution, the reaction mixture was extracted with ethyl acetate and distilled water. The organic layer was dried using anhydrous MgSO$_4$ and then filtered, and the filtrate was concentrated in vacuo. Compound 13 (2.02 g, 98%) was produced as white powder by purifying the resulting mixture on silica gel by column chromatography (ethyl acetate/n-hexane, 1:8 (v/v)).

$^1$H-NMR (400 MHZ, CDCl$_3$) δ 7.63 (d, J=9.5 Hz, 1H), 7.37 (d, J=8.4 Hz, 1H), 7.29 (d, J=8.4 Hz, 2H), 6.91 (d, J=2.3 Hz, 1H), 6.88 (d, J=8.7 Hz, 2H), 6.86 (d, J=8.4 Hz, 1H), 6.25 (d, J=9.4 Hz, 1H), 5.03 (s, 2H), 0.98 (s, 9H), 0.20 (s, 6H).

1.14. Preparation of 7-((4-hydroxybenzyl)oxy)-2H-chromen-2-one (14)

[Compound 14]

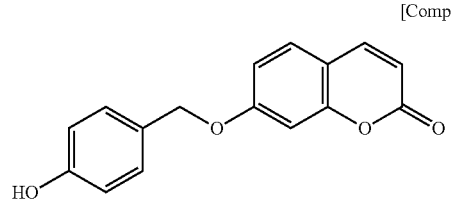

After dissolving Compound 13 (1.00 g, 2.61 mmol) in anhydrous tetrahydrofuran (26.1 mL) under argon gas, acetic acid (1.05 mL, 18.3 mmol) and tetrabutylammonium fluoride (1 M solution in THF, 13 mL, 13 mmol) were sequentially added slowly at 0° C. The reaction mixture was warmed to room temperature and then stirred for 3 hours. Compound 14 (635 mg, 91%) was produced as white powder by concentrating the reaction mixture in vacuo and purifying on silica gel by column chromatography (acetone/n-hexane, 1:2 (v/V)).

$^1$H-NMR (400 MHZ, Acetone-D6) δ 7.89 (d, J=9.5 Hz, 1H), 7.68 (d, J=9.3 Hz, 1H), 7.35 (d, J=8.5 Hz, 2H), 6.98-6.96 (m, 2H), 6.87 (d, J=8.5 Hz, 2H), 6.21 (d, J=9.5 Hz, 1H), 5.13 (s, 2H).

1.15. Preparation of 4-nitrobenzyl (4S,5R,6S)-6-((R)-1-((tert-butylmethylsilyl)oxy)ethyl)-4-methyl-7-oxo-3-((4-(((2-oxo-2H-chromen-7-yl)oxy)methyl) phenoxy)methyl)-1-azabicyclo[3.2.0]hept-2-ene-2-carboxylate (15)

[Compound 15]

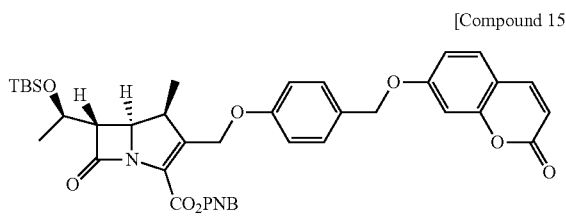

After dissolving the alcohol compound (Compound 6, 129 mg, 0.263 mmol) in toluene (5.3 mL), the phenol compound (Compound 14, 77.6 mg, 0.289 mmol) and triphenylphosphine (92.2 mg, 0.316 mmol) were added at 0° C. After stirring for 2 minutes, diisopropyl azodicarboxylate (67 μL, 0.394 mmol) was added to the mixture. The reaction mixture was warmed to room temperature and then stirred for 30 minutes. After terminating reaction using an aqueous ammonium chloride solution, the reaction mixture was extracted with ethyl acetate and distilled water. The organic layer was dried by adding anhydrous MgSO$_4$ and then filtered, and the filtrate was concentrated in vacuo. Compound 15 (76 mg, 46%) was produced as white powder by purifying the resulting mixture on silica gel by column chromatography (ethyl acetate/n-hexane/chloroform, 2:5:4 (v/v)).

$^1$H-NMR (400 MHZ, CDCl$_3$) δ 8.21 (d, J=8.7 Hz, 2H), 7.66 (d, J=9.0 Hz, 2H), 7.63 (d, J=9.8 Hz, 1H), 7.37 (d, J=8.5 Hz, 1H), 7.35 (d, J=8.6 Hz, 2H), 6.93 (d, J=8.7 Hz, 2H), 6.91-6.87 (m, 2H), 6.25 (d, J=9.4 Hz, 1H), 5.47 (d, J=14.6 Hz, 1H), 5.47 (d, J=13.8 Hz, 1H), 5.27 (d, J=13.8 Hz, 1H), 5.05 (s, 2H), 4.72 (d, J=15.1 Hz, 1H), 4.29-4.25 (m, 2H), 3.50-3.42 (m, 1H), 3.30 (dd, J=3.2, 5.2 Hz, 1H), 1.24 (d, J=6.2 Hz, 6H), 0.86 (s, 9H), 0.09 (s, 3H), 0.07 (s, 3H).

1.16. Preparation of 4-nitrobenzyl (4S,5R,6S)-6-((R)-1-hydroxyethyl)-4-methyl-7-oxo-3-((4-(((2-oxo-2H-chromen-7-yl)oxy)methyl) phenoxy)methyl)-1-azabicyclo[3.2.0]hept-2-ene-2-carboxylate (16)

[Compound 16]

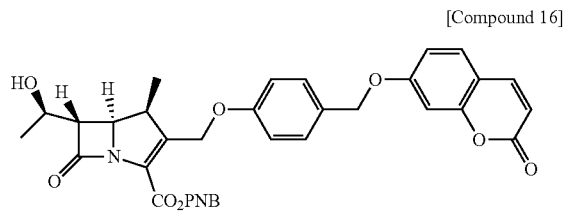

After dissolving the silyl ether compound (Compound 15, 95.0 mg, 0.128 mmol) in a 1:3 mixture of N-methyl-2-pyrrolidinone and dimethylformamide (2.4 mL), ammonium hydrogen fluoride (29.3 mg, 0.513 mmol) was added. The reaction mixture was stirred at room temperature for 30 hours. After terminating reaction with an aqueous sodium bicarbonate solution, the mixture was extracted with ethyl acetate and distilled water. The organic layer was dried by adding anhydrous MgSO$_4$ and then filtered, and the filtrate was concentrated in vacuo. Compound 16 (58.0 mg, 72%) was produced as white powder by purifying the resulting mixture on silica gel by column chromatography (ethyl acetate/n-hexane, 3:1 (v/V)).

$^1$H-NMR (400 MHZ, CDCl$_3$) δ 8.22 (d, J=8.8 Hz, 2H), 7.67-7.62 (m, 3H), 7.38-7.33 (m, 3H), 6.92-6.89 (m, 3H), 6.86 (d, J=2.2 Hz, 1H), 6.25 (d, J=9.4 Hz, 1H), 5.52 (d, J=13.6 Hz, 1H), 5.47 (d, J=14.8 Hz, 1H), 5.26 (d, J=13.8 Hz, 1H), 5.06 (s, 2H), 4.74 (d, J=14.8 Hz, 1H), 4.29-4.24 (m, 2H), 3.52-3.44 (m, 1H), 3.33 (dd, J=3.0, 6.3 Hz, 1H), 1.35 (d, J=6.2 Hz, 3H), 1.25 (d, J=7.2 Hz, 3H).

1.17. Preparation of (4S,5R,6S)-6-((R)-1-hydroxyethyl-4-methyl-7-oxo-3-((4-(((2-oxo-2H-chromen-7-yl)oxy) methyl) phenoxy)methyl)-1-azabicyclo[3.2.0]hept-2-ene-2-carboxylic acid (OMCL01203)

[Compound OMCL01203]

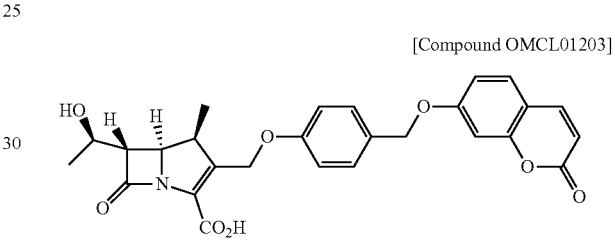

After dissolving Compound 16 (26.0 mg, 0.041 mmol) and 5% Rh/C (2.6 mg) in a 2:1 mixture of tetrahydrofuran and an aqueous solution (1.4 mL) at 0° C., the mixture was warmed to room temperature. After stirring for 2 hours under hydrogen gas, the reaction mixture was filtered using a PTFE syringe filter. Compound OMCL01203 (10.0 mg, 50%) was produced as white powder by purifying the filtrate by preparative RP-HPLC (acetonitrile/aqueous solution, 2:8 to 100:0 (v/v)) and then freeze-drying under reduced pressure.

$^1$H-NMR (400 MHZ, CD$_3$OD) δ 7.87 (d, J=9.6 Hz, 1H), 7.52 (d, J=9.3 Hz, 1H), 7.35 (d, J=8.5 Hz, 2H), 6.98-6.96 (m, 4 H), 6.23 (d, J=9.5 Hz, 1H), 5.54 (d, J=13.5 Hz, 1H), 5.08 (s, 2H), 4.68 (d, J=13.4 Hz, 1H), 4.08-4.02 (m, 2H), 3.47-3.46 (m, 1H), 3.17 (dd, J=2.8, 7.5 Hz, 1H), 3.12-3.11 (m, 1H), 1.25 (d, J=6.3 Hz, 3H), 1.17 (d, J=7.1 Hz, 3H).

1.18. Preparation of 4-nitro-(4S,5R,6S)-6-((R)-1-((tert-butylmethylsilyl)oxy)ethyl)-4-methyl-7-oxo-3-((E)-3-(4-(((2-oxo-2H-chromen-7-yl)oxy)methyl) phenoxy) prop-1-en-1-yl)-1-azabicyclo[3.2.0]hept-2-ene-2-carboxylate (18)

[Compound 18]

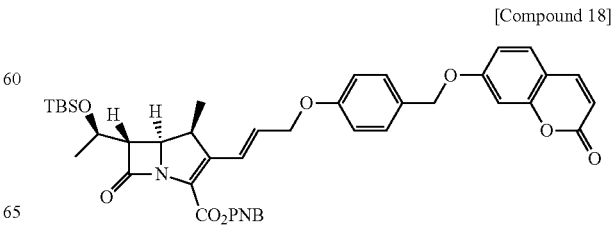

After dissolving the allyl alcohol compound (Compound 7, 20 mg, 0.039 mmol) in toluene ((0.8 mL), the phenol compound (Compound 14, 11.5 mg, 0.043 mmol) and triphenylphosphine (13.7 mg, 0.047 mmol) were added at 0° C. After stirring for 2 minutes, diisopropyl azodicarboxylate (9.8 µL, 0.058 mmol) was added to the mixture. The reaction mixture was warmed to room temperature and then stirred for 30 minutes. After terminating reaction using an aqueous ammonium chloride solution, the reaction mixture was extracted with ethyl acetate and distilled water. The organic layer was dried by adding anhydrous MgSO$_4$ and then filtered. The solvent was removed from the filtrate in vacuo. Compound 18 (22 mg, 74%) was produced as white powder by purifying the resulting mixture on silica gel by column chromatography (ethyl acetate/n-hexane/chloroform, 2:5:4 (v/v)).

$^1$H-NMR (400 MHZ, CDCl$_3$) δ 8.21 (d, J=8.7 Hz, 2H), 7.66 (d, J=8.7 Hz, 2H), 7.63 (d, J=9.5 Hz, 1H), 7.43 (d, J=16.3 Hz, 1H), 7.38-7.34 (m, 3H), 6.93-6.84 (m, 4H), 6.25 (d, J=9.5 Hz, 1H), 6.24-6.19 (m, 1H), 5.44 (d, J=13.9 Hz, 1H), 5.27 (d, J=13.9 Hz, 1H), 5.05 (s, 2H), 4.69 (d, J=5.7 Hz, 2H), 4.27-4.24 (m, 1H), 4.20 (dd, J=2.6, 9.4 Hz, 1H), 3.43-3.35 (m, 1H), 3.24 (dd, J=2.6, 5.6 Hz, 1H), 1.26 (d, J=6.2 Hz, 3H), 1.23 (d, J=7.3 Hz, 3H), 0.86 (s, 9H), 0.08 (s, 3H), 0.06 (s, 3H).

1.19. Preparation of 4-nitrobenzyl (4S,5R,6S)-6-((R)-1-hydroxyethyl)-4-methyl-7-oxo-3-((E)-3-(4-(((2-oxo-2H-chromen-7-yl)oxy)methyl) phenoxy) prop-1-en-1-yl)-1-azabicyclo[3.2.0]hept-2-ene-2-carboxylate (19)

[Compound 19]

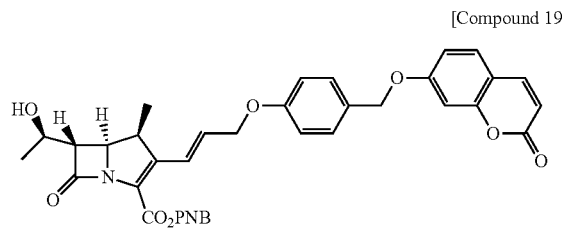

After dissolving the silyl ether compound (Compound 18, 44.0 mg, 0.057 mmol) in a 1:3 mixture of N-methyl-2-pyrrolidinone and dimethylformamide (1:2 mL), ammonium hydrogen fluoride (13.1 mg, 0.229 mmol) was added. The reaction mixture was stirred at room temperature for 30 hours. After terminating reaction with an aqueous sodium bicarbonate solution, the mixture was extracted with ethyl acetate and distilled water. The organic layer was dried by adding anhydrous MgSO$_4$ and then filtered, and the filtrate was concentrated in vacuo. Compound 19 (17.0 mg, 51%) was produced as white powder by purifying the resulting mixture on silica gel by column chromatography (ethyl acetate/n-hexane, 3:1 (v/v)).

$^1$H-NMR (400 MHZ, CDCl$_3$) δ 8.21 (d, J=8.6 Hz, 2H), 7.66 (d, J=8.8 Hz, 2H), 7.63 (d, J=9.7 Hz, 1H), 7.43 (d, J=16.5 Hz, 1H), 7.38-7.33 (m, 3H), 6.92-6.85 (m, 4H), 6.26-6.19 (m, 2H), 5.48 (d, J=13.8 Hz, 1H), 5.25 (d, J=13.8 Hz, 1H), 5.05 (s, 2H), 4.69 (d, J=5.4 Hz, 2H), 4.28-4.21 (m, 2H), 3.48-3.41 (m, 1H), 3.28 (dd, J=2.4, 6.7 Hz, 1H), 1.38 (d, J=6.2 Hz, 3H), 1.24 (d, J=7.5 Hz, 3H).

1.20. Preparation of (4S,5R,6S)-6-((R)-1-hydroxyethyl)-4-methyl-7-oxo-3-((E)-3-(4-(((2-oxo-2H-chromen-7-yl)oxy) methyl) phenoxy) prop-1-en-1-yl)-1-azabicyclo[3.2.0]hept-2-ene-2-carboxylic acid (OMCL01204)

[Compound OMCL01204]

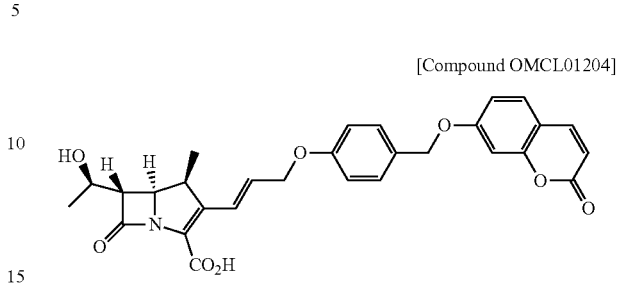

After dissolving Compound 19 (36.0 mg, 0.066 mmol) and 5% Rh/C (4.2 mg) in a 2:1 mixture of tetrahydrofuran and an aqueous solution (2.1 mL) at 0° C., the mixture was warmed to room temperature. After stirring for 2 hours under hydrogen gas, the reaction mixture was filtered using a PTFE syringe filter. Compound OMCL01204 (12.0 mg, 44%) was produced as white powder by purifying the filtrate by preparative RP-HPLC (acetonitrile/aqueous solution, 2:8 to 100:0 (v/v)) and then freeze-drying under reduced pressure.

$^1$H-NMR (400 MHZ, CD$_3$OD) δ 7.87 (d, J=9.4 Hz, 1H), 7.52 (d, J=9.2 Hz, 1H), 7.42 (d, J=16.2 Hz, 1H), 7.35 (d, J=8.4 Hz, 2H), 6.98-6.95 (m, 4H), 6.22 (d, J=9.5 Hz, 1H), 6.01 (dt, J=6.0, 16.1 Hz, 1H), 5.09 (s, 2H), 4.65 (d, J=5.4 Hz, 2H), 4.08-4.03 (m, 2H), 3.14-3.12 (m, 2H), 1.28 (d, J=6.3 Hz, 3H), 1.15 (d, J=7.2 Hz, 3H).

1.21. Preparation of 4-nitrobenzyl (4S,5R,6S)-6-((R)-1-((tert-butyldimethylsilyl)oxy)ethyl)-4-methyl-7-oxo-3-(((((2-oxo-4-(trifluoromethyl)-2H-chromen-7-yl) carbamoyl))methyl)-1-azabicyclo[3.2.0]hept-2-ene-2-carboxylate (21)

[Compound 21]

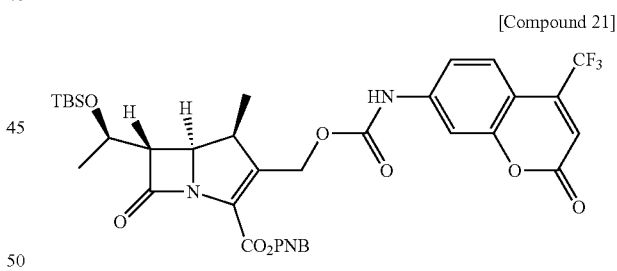

After dissolving 7-amino-4-trifluoromethylcoumarin (50.0 mg, 0.218 mmol) in anhydrous dichloromethane (2.2 mL), triethylamine (60 µL, 0.436 mmol) was added. After slowly adding triphosgene (65.0 mg, 0.218 mmol) 10 minutes later, the reaction mixture was stirred at 90° C. for 6 hours. The resulting mixture was concentrated in vacuo and used in the next reaction without purification. The isocyanate mixture, which is an intermediate, was dissolved in anhydrous tetrahydrofuran (0.5 mL) and the alcohol compound (Compound 6, 27.0 mg, 0.055 mmol) and triethylamine (23 µL, 0.165 mmol) were added. The reaction mixture was stirred at room temperature for 12 hours. Compound 21 (32.0 mg, 78%) was produced as bright yellow powder by concentrating the resulting mixture in vacuo and then purifying on silica gel by column chromatography (ethyl acetate/n-hexane/chloroform, 1:4:3 (v/v)).

¹H-NMR (400 MHZ, CDCl₃) δ 8.21 (d, J=8.7 Hz, 2H), 7.66-7.62 (m, 4H), 7.33 (dd, J=2.0, 8.9 Hz, 1H), 7.01 (s, 1H), 6.68 (s, 1H), 5.60 (d, J=14.1 Hz, 1H), 5.46 (d, J=13.8 Hz, 1H), 5.28 (d, J=13.8 Hz, 1H), 4.94 (d, J=14.1 Hz, 1H), 4.30-4.25 (m, 2H), 3.34-3.28 (m, 2H), 1.24-1.22 (m, 6H), 0.85 (s, 9H), 0.08 (s, 3H), 0.06 (s, 3H).

1.22. Preparation of 4-nitrobenzyl (4S,5R,6S)-6-((R)-1-hydroxyethyl)-4-methyl-7-oxo-3-((((2-oxo-4-(trifluoromethyl)-2H-chromen-7-yl) carbamoyl)oxy)methyl)-1-azabicyclo[3.2.0]hept-2-ene-2-carboxylate (22)

[Compound 22]

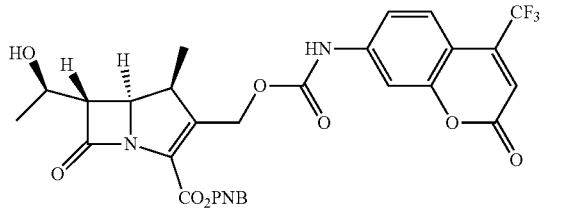

After dissolving the silyl ether compound (Compound 21, 23.9 mg, 0.032 mmol) in a 1:3 mixture of N-methyl-2-pyrrolidinone and dimethylformamide (0.6 mL), ammonium hydrogen fluoride (7.4 mg, 0.120 mmol) was added. The reaction mixture was stirred at room temperature for 30 hours. After terminating reaction with an aqueous sodium bicarbonate solution, the mixture was extracted with ethyl acetate and distilled water. The organic layer was dried by adding anhydrous MgSO₄ and then filtered, and the filtrate was concentrated in vacuo. Compound 22 (8.0 mg, 40%) was produced as white powder by purifying the resulting mixture on silica gel by column chromatography (ethyl acetate/n-hexane, 2:1 (v/v)).

¹H-NMR (400 MHZ, CDCl₃) δ 8.22 (d, J=8.6 Hz, 2H), 7.67-7.62 (m, 4H), 7.33 (dd, J=1.9, 8.8 Hz, 1H), 7.10 (s, 1H), 6.69 (s, 1H), 5.58 (d, J=14.2 Hz, 1H), 5.50 (d, J=13.6 Hz, 1H), 5.27 (d, J=13.7 Hz, 1H), 4.95 (d, J=14.2 Hz, 1H), 4.31-4.25 (m, 2H), 3.39-3.31 (m, 2H), 1.35 (d, J=6.2 Hz, 3H), 1.24 (d, J=7.2 Hz, 3H).

1.23. Preparation of (4S,5R,6S)-6-((R)-1-hydroxyethyl)-4-methyl-7-oxo-3-((((2-oxo-4-(trifluoromethyl)-2H-chromen-7-yl) carbamoyl)oxy)methyl)-1-azabicyclo[3.2.0]hept-2-ene-2-carboxylic acid (OMCL01205)

[Compound OMCL01205]

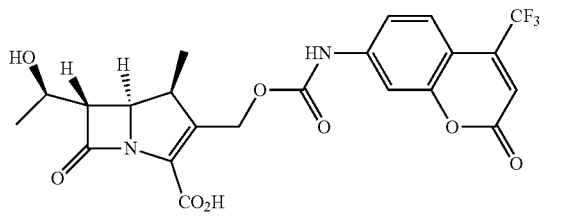

After dissolving Compound 22 (25.0 mg, 0.040 mmol) and 5% Rh/C (2.1 mg) in a 2:1 mixture of tetrahydrofuran and an aqueous solution (1.2 mL) at 0° C., the mixture was warmed to room temperature. After stirring for 2 hours under hydrogen gas, the mixture was filtered using a PTFE syringe filter. Compound OMCL01205 (7.0 mg, 35%) was produced as white powder by purifying the filtrate by preparative RP-HPLC (acetonitrile/aqueous solution, 2:8 to 100:0 (v/v)) and then freeze-drying under reduced pressure.

¹H-NMR (400 MHZ, CD₃OD) δ 7.77 (d, J=2.1 Hz, 1H), 7.70-7.67 (m, 1H), 7.46 (dd, J=2.1, 8.9 Hz, 1H), 6.75 (s, 1H), 5.56 (d, J=13.5 Hz, 1H), 4.97 (d, J=13.4 Hz, 1H), 4.17-4.09 (m, 2H), 3.26-3.15 (m, 2H), 1.30 (d, J=6.3 Hz, 3H), 1.21 (d, J=7.3 Hz, 3H).

1.24. Preparation of 4-nitrobenzyl (4S,5R,6S)-6-((R)-1-((tert-butyldimethylsilyl)oxy)ethyl)-4-methyl-7-oxo-3-((E)-3-(((2-oxo-4-(trifluoromethyl)-2H-chromen-7-yl) carbamoyl)oxy) prop-1-en-1-yl)-1-azabicyclo[3.2.0]hept-2-ene-2-carboxylate (24)

[Compound 24]

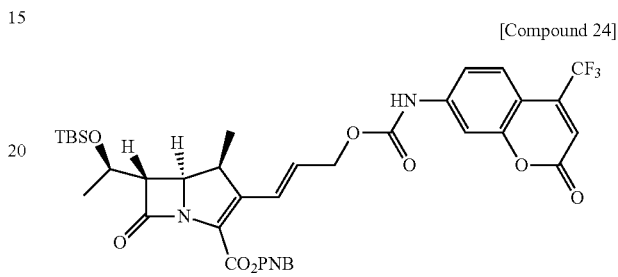

After dissolving 7-amino-4-trifluoromethylcoumarin (99.5 mg, 0.434 mmol) in anhydrous dichloromethane (4.4 mL), triethylamine (133 μL, 0.955 mmol) was added. After slowly adding triphosgene (128.8 mg, 0.434 mmol) 10 minutes later, the reaction mixture was stirred at 90° C. for 6 hours. The resulting mixture was concentrated in vacuo and used in the next reaction without purification. The isocyanate mixture, which is an intermediate, was dissolved in anhydrous tetrahydrofuran (1.0 mL) and then the allyl alcohol compound (Compound 7, 56.3 mg, 0.109 mmol) and triethylamine (46 μL, 0.327 mmol) were added. The reaction mixture was stirred at room temperature for 12 hours. Compound 24 (61.5 mg, 73%) was produced as bright yellow powder by concentrating the resulting mixture in vacuo and then purifying on silica gel by column chromatography (ethyl acetate/n-hexane/chloroform, 1:4:3 (v/v/v)).

¹H-NMR (400 MHZ, CD₃CN) δ 8.33 (s, 1H), 8.11 (d, J=8.7 Hz, 2H), 7.63-7.59 (m, 4H), 7.33 (dd, J=2.1, 8.9 Hz, 1H), 7.27 (d, J=16.4 Hz, 1H), 6.67 (s, 1H), 6.20 (dt, J=5.6, 16.2 Hz, 1H), 5.37 (d, J=14.2 Hz, 1H), 5.24 (d, J=14.1 Hz, 1H), 4.78 (d, J=6.8 Hz, 2H), 4.25-4.18 (m, 2H), 3.46-3.42 (m, 1H), 3.28 (dd, J=3.0, 4.6 Hz, 1H), 1.17-1.14 (m, 6H), 0.80 (s, 9H), 0.05 (s, 3H), 0.01 (s, 3H).

1.25. Preparation of 4-nitrobenzyl (4S,5R,6S)-6-((R)-1-hydroxyethyl)-4-methyl-7-oxo-3-((E)-3-(((2-oxo-4-(trifluoromethyl)-2H-chromen-7-yl) carbamoyl)oxy) prop-1-en-1-yl)-1-azabicyclo[3.2.0]hept-2-ene-2-carboxylate (25)

[Compound 25]

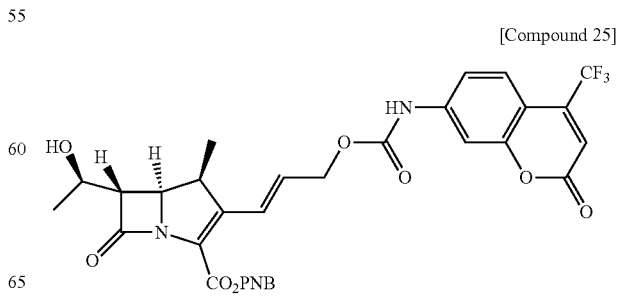

After dissolving the silyl ether Compound 24 (35.0 mg, 0.032 mmol) in a 1:3 mixture of N-methyl-2-pyrrolidinone and dimethylformamide (0.6 mL), ammonium hydrogen fluoride (7.4 mg, 0.120 mmol) was added. The reaction mixture was stirred at room temperature for 30 hours. After terminating reaction with an aqueous sodium bicarbonate solution, the mixture was extracted with ethyl acetate and distilled water. The organic layer was dried by adding anhydrous $MgSO_4$ and then filtered, and the filtrate was concentrated in vacuo. Compound 25 (14.0 mg, 65%) was produced as white powder by purifying the resulting mixture on silica gel by column chromatography (ethyl acetate/n-hexane, 2:1 (v/v)).

$^1$H-NMR (400 MHZ, $CDCl_3$) δ 8.21 (d, J=8.7 Hz, 2H), 7.67-7.62 (m, 4H), 7.39 (d, J=16.0 Hz, 1H), 7.34 (d, J=2.1 Hz, 1H), 6.67 (s, 1H), 6.14 (dt, J=5.9, 16.2 Hz, 1H), 5.48 (d, J=13.8 Hz, 1H), 5.25 (d, J=13.8 Hz, 1H), 4.83 (d, J=5.7 Hz, 2H), 4.28-4.22 (m, 2H), 3.46-3.39 (m, 1H), 3.28 (dd, J=2.6, 6.7 Hz, 1H), 1.37 (d, J=6.2 Hz, 3H), 1.23 (d, J=7.3 Hz, 3H).

1.26. Preparation of (4S,5R,6S)-6-((R)-1-((tert-butyldimethylsilyl)oxy)ethyl)-4-methyl-7-oxo-3-((E)-3-(((2-oxo-4-(trifluoromethyl)-2H-chromen-7-yl) carbamoyl)oxy) prop-1-en-1-yl)-1-azabicyclo[3.2.0]hept-2-ene-2-carboxylic acid (OMCL01206)

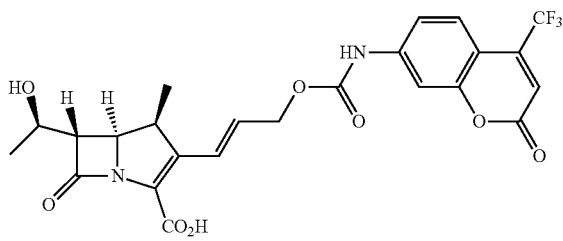

[Compound OMCL01206]

After dissolving Compound 25 (48.0 mg, 0.073 mmol) and 5% Rh/C (3.8 mg) in a 2:1 mixture of tetrahydrofuran and an aqueous solution (1.2 mL) at 0° C., the mixture was warmed to room temperature. After stirring for 2 hours under hydrogen gas, the mixture was filtered using a PTFE syringe filter. Compound OMCL01206 (17.0 mg, 45%) was produced as white powder by purifying the filtrate by preparative RP-HPLC (acetonitrile/aqueous solution, 2:8 to 100:0 (v/v)) and then freeze-drying under reduced pressure.

$^1$H-NMR (400 MHZ, MeOD) δ 7.75 (d, J=2.1 Hz, 1H), 7.64 (dd, J=1.8, 8.9 Hz, 1H), 7.41 (d, J=2.2 Hz, 1H), 7.39 (d, J=2.1 Hz, 1H), 6.71 (s, 1H), 5.97 (dt, J=5.8, 16.3 Hz, 1H), 4.76 (d, J=5.3 Hz, 2H), 4.09-4.03 (m, 2H), 3.34-3.33 (m, 1H), 3.15-3.11 (m, 1H), 1.28 (d, J=6.2 Hz, 3H), 1.17 (d, J=7.2 Hz, 3H).

1.27. Preparation of tert-butyl (2-((tert-butyldimethylsilyl)oxy)benzyl)oxy) dimethylsilane (27)

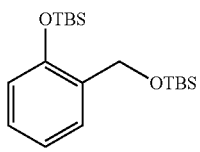

[Compound 27]

After dissolving hydroxybenzyl alcohol (500 mg, 4.03 mmol) in anhydrous dimethylformamide (20.2 mL), imidazole (1.27 g, 10.1 mmol) and tert-butyldimethylsilyl chloride (1.52 g, 10.1 mmol) were added at 0° C. The reaction mixture was warmed to room temperature and then stirred for 12 hours. After terminating reaction using an aqueous ammonium chloride solution, the reaction mixture was extracted with ethyl acetate and an aqueous solution. The organic layer was dried using anhydrous $MgSO_4$ and then filtered, and the filtrate was concentrated in vacuo. Compound 27 (1.08 g, 76%) was produced as colorless oil by purifying the resulting mixture on silica gel by column chromatography (ethyl acetate/n-hexane, 1:15 (v/V)).

$^1$H-NMR (400 MHZ, $CDCl_3$) δ 7.46 (dt, J=1.0, 9.4 Hz, 1H), 7.11 (td, J=2.0, 9.6 Hz, 1H), 6.97 (td, J=1.2, 9.3 Hz, 1H), 6.74 (dd, J=1.2, 10.0 Hz, 1H), 4.76 (s, 2H), 1.01 (s, 9H), 0.95 (s, 9H), 0.22 (s, 6H), 0.10 (s, 6H).

1.28. Preparation of (2-((tert-butyldimethylsilyl)oxy)phenyl) methanol (28)

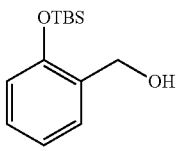

[Compound 28]

After dissolving the silyl ether compound (Compound 27, 636 mg, 1.80 mmol) in acetonitrile (25.8 mL) at room temperature, cerium chloride heptahydrate (13.4 g, 3.61 mmol) was added. After stirring at 90° C. for 12 hours and then terminating reaction using an aqueous ammonium chloride solution, the reaction mixture was extracted with ethyl acetate and an aqueous solution. The organic layer was dried using anhydrous $MgSO_4$ and then filtered, and the filtrate was concentrated in vacuo. Compound 28 (49.0 mg, 72%) was produced as colorless oil by purifying the resulting mixture on silica gel by column chromatography (ethyl acetate/n-hexane, 1:8 to 1:4 (v/v)).

$^1$H-NMR (400 MHZ, $CDCl_3$) δ 7.31 (dd, J=2.0, 9.3 Hz, 1H), 7.18 (td, J=2.1, 9.7 Hz, 1H), 6.96 (dt, J=1.2, 9.3 Hz, 1H), 6.82 (d, J=10.1 Hz, 1H), 4.68 (s, 2H), 1.02 (s, 9H), 0.26 (s, 6H).

1.29. Preparation of 7-((2-((tert-butyldimethylsilyl)oxy)benzyl)oxy)-2H-chromen-2-one (29)

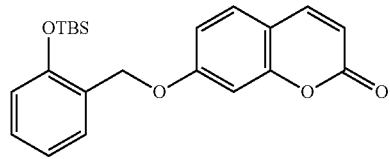

[Compound 29]

After dissolving the benzyl alcohol compound (Compound 28, 68.0 mg, 0.285 mmol) in toluene (5.80 mL), umbelliferone (50.8 mg, 0.314 mmol) and triphenylphosphine (100 mg, 0.342 mmol) were added at 0° C. After stirring for 2 minutes, diisopropyl azodicarboxylate (0.072 mL, 0.428 mmol) was added to the mixture. The reaction mixture was warmed to room temperature and then stirred for 30 minutes. After terminating reaction using an aqueous ammonium chloride solution, the reaction mixture was extracted with ethyl acetate and distilled water. The organic layer was dried by adding anhydrous $MgSO_4$ and then filtered, and the filtrate was concentrated in vacuo. Compound 29 (84.0 mg, 77%) was produced as white powder by purifying the resulting mixture on silica gel by column chromatography (ethyl acetate/n-hexane, 1:8 (v/v)).

$^{1}$H-NMR (400 MHZ, CDCl$_{3}$) δ 7.62 (d, J=11.8 Hz, 1H), 7.39 (dd, J=1.9, 9.5 Hz, 1H), 7.36 (d, J=10.5 Hz, 1H), 7.22 (td, J=2.0, 9.7 Hz, 1H), 6.97 (td, J=1.2, 9.4 Hz, 1H), 6.91-6.85 (m, 3H), 6.24 (d, J=11.8 Hz, 1H), 5.12 (s, 2H), 0.97 (s, 9H), 0.25 (s, 6H).

1.30. Preparation of 7-((2-hydroxybenzyl)oxy)-2H-chromen-2-one (30)

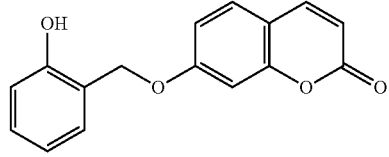

[Compound 30]

After dissolving Compound 29 (427 mg, 1.12 mmol) in anhydrous tetrahydrofuran (11.2 mL) under argon gas, acetic acid (0.447 mL, 7.81 mmol) and tetrabutylammonium fluoride (1 M solution in THF, 5.6 mL, 5.58 mmol) were slowly added sequentially at 0° C. The reaction mixture was warmed to room temperature and then stirred for 3 hours. Compound 30 (292 mg, 98%) was produced as white powder by concentrating the reaction mixture in vacuo and then purifying on silica gel by column chromatography (acetone/n-hexane, 1:2 (v/V)).

$^{1}$H-NMR (400 MHZ, CDCl$_{3}$) δ 7.89 (d, J=11.8 Hz, 1H), 7.58 (d, J=10.4 Hz, 1H), 7.41 (dd, J=1.8, 9.4 Hz, 1H), 7.20 (td, J=1.9, 9.6 Hz, 1H), 7.01-6.98 (m, 2H), 6.94 (d, J=9.4 Hz, 1H), 6.88 (td, J=1.1, 9.3 Hz, 1H), 6.21 (d, J=11.9 Hz, 1H), 5.25 (s, 2H).

1.31. Preparation of 4-nitrobenzyl (4S,5R,6S)-6-((R)-1-((tert-butylmethylsilyl)oxy)ethyl)-4-methyl-7-oxo-3-((2-(((2-oxo-2H-chromen-7-yl)oxy)methyl) phenoxy)methyl)-1-azabicyclo[3.2.0]hept-2-ene-2-carboxylate (31)

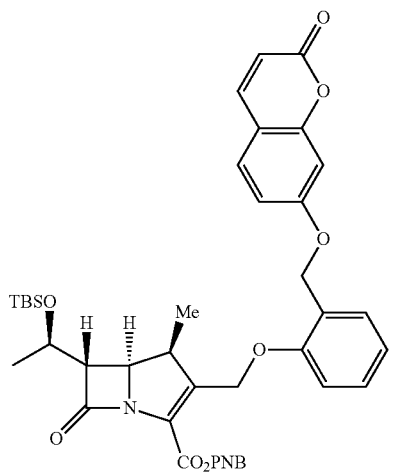

[Compound 31]

After dissolving the alcohol compound (Compound 6, 117 mg, 0.238 mmol) in toluene (4.8 mL), the phenol compound (Compound 30, 70.4 mg, 0.262 mmol) and triphenylphosphine (83.5 mg, 0.286 mmol) were added at 0° C. After stirring for 2 minutes, diisopropyl azodicarboxylate (60 μL, 0.357 mmol) was added to the mixture. The reaction mixture was warmed to room temperature and then stirred for 30 minutes. After terminating reaction using an aqueous ammonium chloride solution, the reaction mixture was extracted with ethyl acetate and distilled water. The organic layer was dried by adding anhydrous MgSO$_{4}$ and then filtered, and the filtrate was concentrated in vacuo. Compound 31 (87.6 mg, 50%) was produced as white powder by purifying the resulting mixture on silica gel by column chromatography (ethyl acetate/n-hexane/chloroform, 2:5:4 (v/v)).

$^{1}$H-NMR (400 MHZ, CDCl$_{3}$) δ 8.22 (d, J=10.8 Hz, 2H), 7.68-7.58 (m, 3H), 7.42 (d, J=9.5 Hz, 1H), 7.37 (d, J=11.6 Hz, 1H), 7.32 (t, J=9.1 Hz, 1H), 7.02 (t, J=9.2 Hz, 1H), 6.95-6.89 (m, 3H), 6.26 (d, J=11.8 Hz, 1H), 5.53 (d, J=18.2 Hz, 1H), 5.48 (d, J=17.2 Hz, 1H), 5.28 (d, J=17.2 Hz, 1H), 5.05 (s, 2H), 4.80 (d, J=18.4 Hz, 1H), 4.27-4.20 (m, 2H), 3.41-3.33 (m, 1H), 3.27 (t, J=5.0 Hz, 1H), 1.21 (d, J=5.8 Hz, 3H), 1.20 (d, J=4.3 Hz, 3H), 0.83 (s, 9H), 0.08 (s, 3H), 0.02 (s, 3H).

1.32. Preparation of 4-nitrobenzyl (4S,5R,6S)-6-((R)-1-hydroxyethyl)-4-methyl-7-oxo-3-((2-(((2-oxo-2H-chromen-7-yl)oxy)methyl) phenoxy)methyl)-1-azabicyclo[3.2.0]hept-2-ene-2-carboxylate (32)

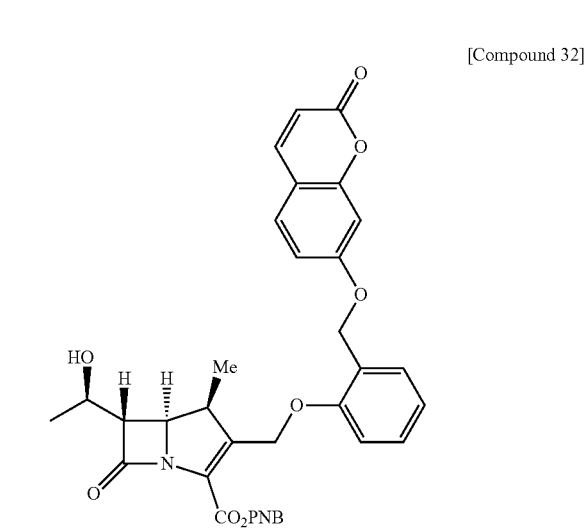

[Compound 32]

After dissolving the silyl ether compound (Compound 31, 69.9 mg, 0.094 mmol) in a 1:3 mixture of N-methyl-2-pyrrolidinone and dimethylformamide (1.9 mL), ammonium hydrogen fluoride (21.6 mg, 0.378 mmol) was added. The reaction mixture was stirred at room temperature for 30 hours. After terminating reaction with an aqueous sodium bicarbonate solution, the mixture was extracted with ethyl acetate and distilled water. The organic layer was dried by adding anhydrous MgSO$_{4}$ and then filtered, and the filtrate was concentrated in vacuo. Compound 32 (28.1 mg, 48%) was produced as white powder by purifying the resulting mixture on silica gel by column chromatography (ethyl acetate/n-hexane, 3:1 (v/V)).

$^{1}$H-NMR (400 MHZ, CDCl$_{3}$) δ 8.21 (d, J=10.8 Hz, 2H), 7.67-7.59 (m, 3H), 7.42 (d, J=9.5 Hz, 1H), 7.37 (d, J=11.6 Hz, 1H), 7.32 (t, J=9.1 Hz, 1H), 7.01 (t, J=9.2 Hz, 1H), 6.96-6.89 (m, 3H), 6.25 (d, J=11.8 Hz, 1H), 5.52 (d, J=18.2 Hz, 1H), 5.48 (d, J=17.2 Hz, 1H), 5.28 (d, J=17.2 Hz, 1H), 5.06 (s, 2H), 4.79 (d, J=18.4 Hz, 1H), 4.28-4.21 (m, 2H), 3.41-3.43 (m, 1H), 3.28 (dd, J=3.0, 6.3 Hz, 1H), 1.35 (d, J=6.2 Hz, 3H), 1.25 (d, J=7.2 Hz, 3H).

1.33. Preparation of (4S,5R,6S)-6-((R)-1-hydroxyethyl)-4-methyl-7-oxo-3-((2-(((2-oxo-2H-chromen-7-yl)oxy)methyl)phenoxy)methyl)-1-azabicyclo[3.2.0]hept-2-ene-2-carboxylic acid (OMCL01207)

[Compound OMCL01207]

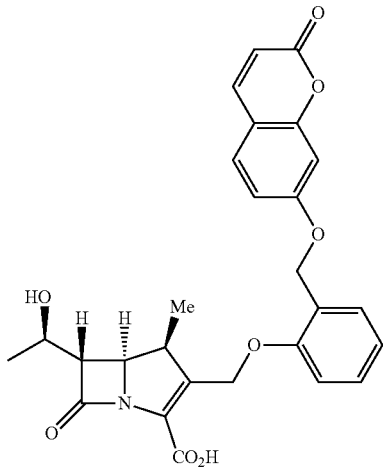

After dissolving Compound 32 (22.0 mg, 0.035 mmol) and 5% Rh/C (2.2 mg) in a 2:1 mixture of tetrahydrofuran and an aqueous solution (1.2 mL) at 0° C., the mixture was warmed to room temperature. After stirring for 2 hours under hydrogen gas, the mixture was filtered using a PTFE syringe filter. Compound OMCL01207 (5.4 mg, 31%) was produced as white powder by purifying the filtrate by preparative RP-HPLC (acetonitrile/aqueous solution, 2:8 to 10:0 (v/v)) and then freeze-drying under reduced pressure.

$^1$H-NMR (400 MHZ, CD$_3$OD) δ 7.82 (d, J=9.5 Hz, 1H), 7.57 (d, J=11.6 Hz, 1H), 7.45 (d, J=9.1 Hz, 1H), 7.39 (d, J=9.2 Hz, 1H), 6.95-6.89 (m, 3H), 6.26 (d, J=11.8 Hz, 1H), 5.53 (d, J=18.2 Hz, 1H), 5.48 (d, J=17.2 Hz, 1H), 5.28 (d, J=17.2 Hz, 1H), 5.05 (s, 2H), 4.80 (d, J=18.4 Hz, 1H), 4.27-4.20 (m, 2H), 3.41-3.33 (m, 1H), 3.27 (t, J=5.0 Hz, 1H), 1.21 (d, J=5.8 Hz, 3H), 1.20 (d, J=4.3 Hz, 3H).

1.34. Preparation of 4-nitrobenzyl (4S,5R,6S)-6-((R)-1-((tert-butyldimethylsilyl)oxy)ethyl)-4-methyl-3-((((4-methyl-2-oxo-2H-chromen-7-yl) carbamoyl)oxy)methyl)-7-oxo-1-azabicyclo[3.2.0]hept-2-ene-2-carboxylate (34)

[Compound 34]

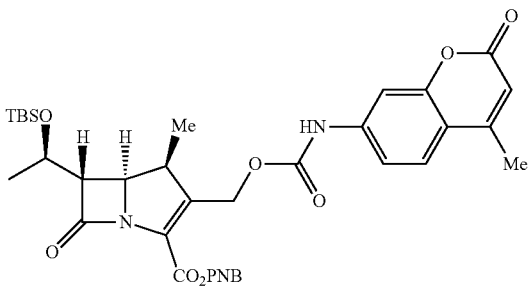

After dissolving 7-amino-4-methylcoumarin (224 mg, 1.28 mmol) in anhydrous dichloromethane (6.4 mL), triethylamine (393 μL, 2.81 mmol) was added. After slowly adding triphosgene (129 mg, 1.28 mmol) 10 minutes later, the reaction mixture was stirred at 90° C. for 6 hours. The resulting mixture was concentrated in vacuo and used in the next reaction without purification. After dissolving the isocyanate mixture, which is an intermediate, in anhydrous tetrahydrofuran (1.6 mL), the alcohol compound (Compound 6, 157 mg, 0.320 mmol) and triethylamine (134 μL, 0.960 mmol) were added. The reaction mixture was stirred at room temperature for 12 hours. Compound 34 (72.0 mg, 33%) was produced as white powder by concentrating the resulting mixture in vacuo and then purifying on silica gel by column chromatography (ethyl acetate/n-hexane/chloroform, 2:4:5 (v/v)).

$^1$H-NMR (400 MHZ, CDCl$_3$) δ 8.21 (dd, J=2.3, 8.6 Hz, 2H), 7.66 (d, J=10.9 Hz, 2H), 7.54 (d, J=10.9 Hz, 1H), 7.41 (d, J=10.1 Hz, 2H), 6.95 (s, 1H), 6.20 (d, J=1.4 Hz, 1H), 5.59 (d, J=17.7 Hz, 1H), 5.46 (d, J=17.2 Hz, 1H), 5.29 (d, J=17.3 Hz, 1H), 4.93 (d, J=17.8 Hz, 1H), 4.29-4.25 (m, 2H), 3.33-3.29 (m, 2H), 2.41 (d, J=1.3 Hz, 3H), 1.23 (d, J=7.6 Hz, 3H), 1.22 (d, J=3.1 Hz, 3H), 0.86 (s, 9H), 0.08 (s, 3H), 0.06 (s, 3H).

1.35. Preparation of 4-nitrobenzyl (4S,5R,6S)-6-((R)-1-hydroxyethyl)-4-methyl-3-((((4-methyl-2-oxo-2H-chromen-7-yl) carbamoyl)oxy)methyl)-7-oxo-1-azabicyclo[3.2.0]hept-2-ene-2-carboxylate (35)

[Compound 35]

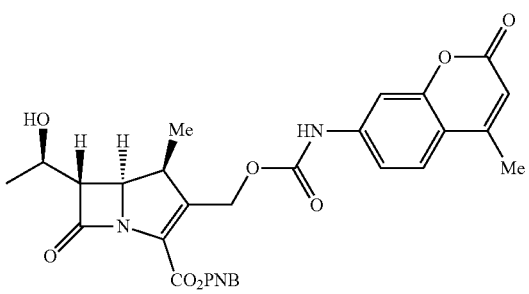

After dissolving the silyl ether compound (Compound 34, 82.0 mg, 0.119 mmol) in a 1:3 mixture of N-methyl-2-pyrrolidinone and dimethylformamide (2.4 mL), ammonium hydrogen fluoride (27.0 mg, 0.474 mmol) was added. The reaction mixture was stirred at room temperature for 30 hours. After terminating reaction with an aqueous sodium bicarbonate solution, the mixture was extracted with ethyl acetate and distilled water. The organic layer was dried by adding anhydrous MgSO$_4$ and then filtered, and the filtrate was concentrated in vacuo. Compound 35 (35.0 mg, 51%) was produced as white powder by purifying the resulting mixture on silica gel by column chromatography (ethyl acetate/n-hexane, 3:1 (v/v)).

$^1$H-NMR (400 MHZ, CDCl$_3$) δ 8.23 (d, J=10.9 Hz, 2H), 7.66 (d, J=10.8 Hz, 2H), 7.54 (d, J=10.8 Hz, 1H), 7.41-7.40 (m, 2H), 6.96 (s, 1H), 6.20 (d, J=1.3 Hz, 1H), 5.58 (d, J=17.8 Hz, 1H), 5.51 (d, J=17.0 Hz, 1H), 5.25 (d, J=17.1 Hz, 1H), 4.93 (d, J=18.1 Hz, 1H), 4.31-4.26 (m, 2H), 3.40-3.26 (m, 2H), 2.38 (d, J=10.2 Hz, 3H), 1.35 (d, J=7.8 Hz, 3H), 1.25 (d, J=9.1 Hz, 3H).

1.36. Preparation of (4S,5R,6S)-6-((R)-1-hydroxyethyl)-4-methyl-3-((((4-methyl-2-oxo-2H-chromen-7-yl) carbamoyl)oxy)methyl)-7-oxo-1-azabicyclo[3.2.0]hept-2-ene-2-carboxylic acid (OMCL01208)

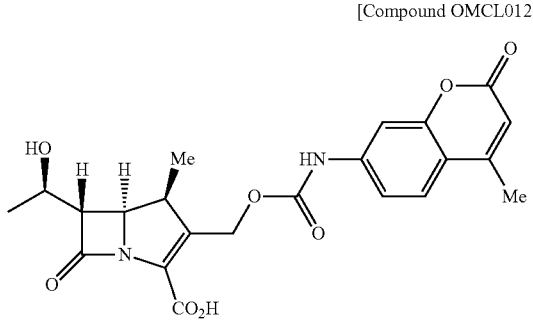

[Compound OMCL01208]

After dissolving Compound 35 (35.0 mg, 0.061 mmol) and 5% Rh/C (3.8 mg) in a 2:1 mixture of tetrahydrofuran and an aqueous solution (2.1 mL) at 0° C., the mixture was warmed to room temperature. After stirring for 2 hours under hydrogen gas, the mixture was filtered using a PTFE syringe filter. Compound OMCL01208 (7.0 mg, 26%) was produced as white powder by purifying the filtrate by preparative RP-HPLC (acetonitrile/aqueous solution, 2:8 to 10:0 (v/V)) and then freeze-drying under reduced pressure.

$^1$H-NMR (400 MHZ, CD$_3$OD) δ 7.71 (d, J=11.0 Hz, 1H), 7.63 (d, J=2.4 Hz, 1H), 7.44 (dd, J=2.5, 10.8 Hz, 1H), 6.22 (s, 1H), 5.55 (d, J=16.9 Hz, 1H), 4.96 (d, J=17.0 Hz, 1H), 4.17-4.10 (m, 2H), 3.24-3.22 (m, 2H), 2.47 (s, 3H), 1.30 (d, J=7.9 Hz, 3H), 1.21 (d, J=9.1 Hz, 3H).

1.37. Preparation of 4-nitrobenzyl (4S,5R,6S)-6-((R)-1-tert-butyldimethylsilyl)oxy)ethyl)-3-formyl-4-methyl-7-oxo-1-azabicyclo[3.2.0]hept-2-ene-2-carboxylate (37)

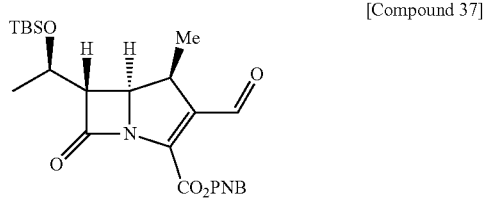

[Compound 37]

After dissolving the alcohol compound (Compound 6, 20.0 mg, 0.041 mmol) in anhydrous dichloromethane (0.3 mL) at 0° C., Dess-Martin periodinane (19.1 mg, 0.045 mmol) was added. The reaction mixture was stirred for 1 hour. After terminating reaction at 5° C. with an aqueous solution, the mixture was extracted with dichloromethane and distilled water. The organic layer was dried by adding anhydrous MgSO$_4$ and then filtered, and the filtrate was concentrated in vacuo. Compound 37 (12.7 mg, 64%) was produced as bright yellow powder by purifying the resulting mixture on silica gel by column chromatography (ethyl acetate/n-hexane, 1:8 (v/v)).

$^1$H-NMR (400 MHZ, CDCl$_3$) δ 10.4, (s, 1H), 8.24 (d, J=10.8 Hz, 2H), 7.66 (d, J=10.8 Hz, 2H), 5.50 (d, J=17.1 Hz, 1H), 5.36 (d, J=17.1 Hz, 1H), 4.36 (dd, J=4.3, 13.0 Hz, 1H), 4.33-4.27 (m, 1H), 3.55-3.47 (m, 1H), 3.41 (t, J=5.0 Hz, 1H), 1.24 (d, J=9.4 Hz, 3H), 1.22 (d, J=8.0 Hz, 3H), 0.85 (s, 9H), 0.10 (s, 3H), 0.06 (s, 3H).

1.38. Preparation of 4-nitrobenzyl (4S,5R,6S)-6-((R)-1-((tert-butyldimethylsilyl)oxy)ethyl)-4-methyl-3-((((4-methyl-2-oxo-2H-chromen-7-yl)amino)methyl)-7-oxo-1-azabicyclo[3.2.0]hept-2-ene-2-carboxylate (38)

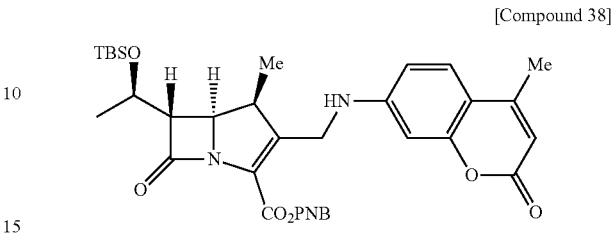

[Compound 38]

After dissolving 7-amino-4-methylcoumarin (56.7 mg, 0.324 mmol) in anhydrous dichloromethane (1.7 mL), the aldehyde compound (Compound 37, 105.4 mg, 0.216 mmol) and acetic acid (2 μL, 0.216 mmol) were added. After stirring for 3 hours and adding sodium triacetoxyborohydride (137 mg, 0.648 mmol), the reaction mixture was stirred at room temperature for 12 hours. After terminating reaction with an aqueous sodium bicarbonate solution, the mixture was extracted with ethyl acetate and distilled water. The organic layer was dried by adding anhydrous MgSO$_4$ and then filtered, the filtrate was concentrated in vacuo. Compound 38 (66.6 mg, 48%) was produced as yellow powder by purifying the resulting mixture on silica gel by column chromatography (ethyl acetate/n-hexane, 1:2 (v/V)).

$^1$H-NMR (400 MHZ, CDCl$_3$) δ 8.20 (d, J=10.7 Hz, 2H), 7.67 (d, J=10.6 Hz, 2H), 7.34 (d, J=11.2 Hz, 1H), 6.58-6.50 (m, 3H), 5.98 (s, 1H), 5.48 (d, J=17.4 Hz, 1H), 5.30 (d, J=17.4 Hz, 1H), 4.72 (d, J=20.4 Hz, 1H), 4.24 (t, J=7.1 Hz, 1H), 4.18 (dd, J=3.5, 12.8 Hz, 1H), 3.98 (d, J=20.5 Hz, 1H), 3.26-3.17 (m, 2H), 2.33 (s, 3H), 1.20 (d, J=8.2 Hz, 6H), 0.83 (s, 9H), 0.06 (s, 3H), 0.04 (s, 3H).

1.39. Preparation of 4-nitrobenzyl (4S,5R,6S)-6-((R)-1-hydroxyethyl)-4-methyl-3-((((4-methyl-2-oxo-2H-chromen-7-yl)amino)methyl)-7-oxo-1-azabicyclo[3.2.0]hept-2-ene-2-carboxylate (39)

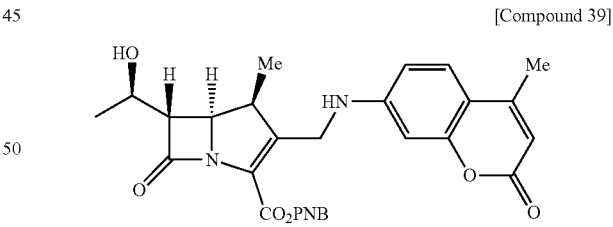

[Compound 39]

After dissolving the silyl ether compound (Compound 38, 107 mg, 0.155 mmol) in a 1:3 mixture of N-methyl-2-pyrrolidinone and dimethylformamide (3.2 mL), ammonium hydrogen fluoride (35.4 mg, 0.621 mmol) was added. The reaction mixture was stirred at room temperature for 30 hours. After terminating reaction with an aqueous sodium bicarbonate solution, the mixture was extracted with ethyl acetate and distilled water. The organic layer was dried by adding anhydrous MgSO$_4$ and then filtered, and the filtrate was concentrated in vacuo. Compound 39 (48.1 mg, 54%) was produced as bright yellow powder by purifying the resulting mixture on silica gel by column chromatography (ethyl acetate/n-hexane, 3:1 (v/v)).

$^{1}$H-NMR (400 MHZ, CDCl$_3$) δ 8.18 (d, J=10.8 Hz, 2H), 7.65 (d, J=10.8 Hz, 2H), 7.30 (d, J=10.8 Hz, 1H), 6.48 (dd, J=2.8, 10.8 Hz, 1H), 6.42 (d, J=2.7 Hz, 1H), 5.95 (s, 1H), 5.51 (d, J=17.42 Hz, 1H), 5.25 (d, J=17.2 Hz, 1H), 4.71 (d, J=20.8 Hz, 1H), 4.19-4.15 (m, 2H), 3.95 (d, J=20.9 Hz, 1H), 3.25-3.18 (m, 2H), 2.33 (s, 3H), 1.29 (d, J=7.8 Hz, 3H), 1.18 (d, J=9.1 Hz, 3H).

1.40. Preparation of (4S,5R,6S)-6-((R)-1-hydroxyethyl)-4-methyl-3-((((4-methyl-2-oxo-2H-chromen-7-yl)amino)methyl)-7-oxo-1-azabicyclo[3.2.0]hept-2-ene-2-carboxylic acid (OMCL01209)

[Compound OMCL01209]

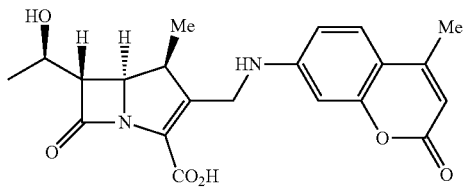

After dissolving Compound 39 (40.5 mg, 0.076 mmol) and 5% Rh/C (6.4 mg) in a 2:1 mixture of tetrahydrofuran and an aqueous solution (2.4 mL) at 0° C., the mixture was warmed to room temperature. After stirring for 2 hours under hydrogen gas, the mixture was filtered using a PTFE syringe filter. Compound OMCL01209 (7.3 mg, 24%) was produced as white powder by purifying the filtrate by preparative RP-HPLC (acetonitrile/aqueous solution, 2:8 to 10:0 (v/v)) and then freeze-drying under reduced pressure.

$^{1}$H-NMR (400 MHZ, CD$_3$OD) δ 7.46 (d, J=11.1 Hz, 1H), 6.67 (dd, J=2.5, 10.9 Hz, 1H), 6.48 (d, J=2.5 Hz, 1H), 5.91 (s, 1H), 5.48 (s, 1H), 4.78 (d, J=20.1 Hz, 1H), 4.04 (t, J=8.5 Hz, 1H), 3.98 (dd, J=3.4, 12.3 Hz, 1H), 3.88 (d, J=20.2 Hz, 1H), 3.13-3.05 (m, 2H), 2.36 (s, 3H), 1.24 (d, J=7.8 Hz, 3H), 1.14 (d, J=9.1 Hz, 3H).

Example 2: Detection of Antibiotic-Resistant Bacteria from Clinical Sample

The detection efficiency of carbapenemase-producing carbapenem-resistant bacteria of a control probe OMCL01201 (CPC-1 described in Chinese Patent Publication No. CN106279178A) and the OMCL01203 probe of the present disclosure was evaluated at Gangnam St. Mary's Hospital for the bacteria described in Table 1.

Briefly, 10 μL of a sample was lysed with a Tris-HCl buffer (B-PER, Thermo Scientific Pierce) and then vortexed for 1 minute. After culturing for 30 minutes at room temperature and centrifuging for 5 minutes (10,000 g), 30 μL of the supernatant was reacted with 100 μL of PBS and 13 μL of the fluorescent probe (1 mM). Then, fluorescence was measured for 50 minutes with 5-minute intervals using a fluorescence plate reader (Infinite F200pro, Tecan Group Ltd.).

TABLE 1

| Carbapenemase class and gene | No. of isolates | CPC-1 result(s) | Pos. % | OMCL01203 result(s) | Pos. % |
|---|---|---|---|---|---|
| Ambler class A (39) | | | | | |
| KPC | 33 | 15 | 45% | 33 | 100% |
| GES | 2 | 0 | 0% | 2 | 100% |
| Ambler class B (17) | | | | | |
| NDM | 9 | 8 | 89% | 8 | 89% |
| VIM | 7 | 3 | 43% | 7 | 100% |
| IMP | 1 | 0 | 0% | 1 | 100% |
| Ambler class D (6) | | | | | |
| OXA | 6 | 1 | 17% | 5 | 83% |
| co-producing (3) | | | | | |
| KPC/OXA | 2 | | 0% | 2 | 100% |
| NDM/OXA | 1 | 1 | 100% | 1 | 100% |
| CPE total | 61 | 28 | 46% | 59 | 97% |
| Non-CP CRE (40) | 40 | 0 | 0% | 0 | 0% |

As a result, the control probe CPC-1 determined 28 out of 61 CPE (carbapenemase-producing Enterobacteriaceae) species (46%) as positive, and determined all 40 non-CPE species as negative.

In contrast, the OMCL01203 probe determined 59 out of the 61 CPE species (97%) as positive, and determined all the 40 non-CPE species as negative.

In addition, the detection efficiency of the fluorescence detection method using the OMCL01203 probe was compared for carbapenemase-producing carbapenem-resistant bacteria (CP-CRE) and non-carbapenemase-producing carbapenem-resistant bacteria (non-CP-CRE) with mCIM, CarbaNP and CIT methods. The result is shown in Table 2.

As a result, the fluorescence detection method using the OMCL01203 probe determined only 3 out of 65 positive bacteria as false positive, and determined all negative bacteria as negative.

In contrast, the mCIM method showed a higher false-negative rate, the CarbNP method showed a higher false-positive rate, and the CIT method showed higher false-positive and false-negative rates, when compared with the fluorescence detection method using the OMCL01203 probe.

Accordingly, it was confirmed from the above results that the probe developed in the present disclosure has superior detection ability.

Although the specific exemplary embodiments of the present disclosure have been described in detail, it will be obvious to those having ordinary knowledge in the art that they are only preferred exemplary embodiments and the scope of the present disclosure is not limited by them. Thus, the substantial scope of the present disclosure is limited by the appended claims and their equivalents.

TABLE 2

| | | No. of isolates | MICs (μg/ml) | | | Fluore result | mCIM result | CNP result | CIT result |
|---|---|---|---|---|---|---|---|---|---|
| | | | Carbapenemase class and gene | | | | | | |
| | Species | No. of isolates | IPM | MEM | ERT | Fluore result | mCIM result | CNP result | CIT result |
| CPE (65) | | | | | | | | | |
| Ambler Class A (39) | | | | | | | | | |
| KPC (36) | Citrobacter freundii | 1 | >16 | 8 | >16 | Pos | Pos | Pos | Pos-A |
| | Escherichia coli | 3 | 2 to 8 | 4 | 8 | Pos | Pos | Pos | Pos-A |
| | Klebsiella aerogenes | 1 | >16 | 16 | >16 | Pos | Pos | Pos | Pos-A |
| | Klebsiella oxytoca | 1 | >16 | >16 | >16 | Pos | Pos | Pos | Pos-A |
| | Klebsiella pneumoniae | 30 | 4 to >16 | 8 to >16 | 16 to >16 | Pos | Pos | Pos | Pos-A |
| GES (3) | Escherichia coli | 2 | 1 to >16 | 2 to >16 | 8 to >16 | Pos | Neg | Neg(2) | A(1); Pos-Neg(1) |
| | Klebsiella pneumoniae | 1 | >16 | >16 | >16 | Neg(1) | Neg | Neg(1) | Pos-A |
| Ambler Class B (17) | | | | | | | | | |
| NDM (9) | Citrobacter freundii | 1 | 8 | 16 | >16 | Pos | Pos | Pos-B | Pos-B |
| | Enterobacter cloacae | 2 | >16 | >16 | >16 | Pos | Pos | Pos-B | Pos-B |
| | Escherichia coli | 4 | 8 to 16 | >16 | >16 | Pos | Pos | Pos-B | Pos-B |
| | Klebsiella pneumoniae | 1 | >16 | >16 | >16 | Pos | Pos | Pos-B | Pos-B |
| | Morganella morganii | 1 | >16 | 4 | 2 | Pos | Pos | Pos-B | Pos-B |
| VIM (7) | Citrobacter freundii | 4 | 0.5 to >16 | 16 to >16 | 2 to >16 | Pos | Pos | Pos-B(3); Neg(1) | Pos-B(3); Neg(1) |
| | Enterobacter cloacae | 1 | 4 | 2 | 1 | Pos | Pos | Neg(1) | Pos-B |
| | Klebsiella oxytoca | 1 | 2 | 1 | 0.5 | Pos | Pos | Neg(1) | Neg(1) |
| | Klebsiella pneumoniae | 1 | >16 | >16 | >16 | Pos | Pos | Pos-B | Pos-B |
| IMP (1) | Escherichia coli | 1 | 1 | 1 | 4 | Pos | Pos | Neg(1) | Neg(1) |
| Ambler Class D (6) | | | | | | | | | |
| OXA (6) | Citrobacter freundii | 1 | 2 | 0.5 | 1 | Pos | Pos | Neg(1) | Neg(1) |
| | Escherichia coli | 3 | 0.5 to 8 | ≤0.25 to 4 | ≤0.125 to >16 | Pos(1); Neg(2) | Pos(2) Neg(1) | Neg(3) | Neg(3) |
| | Klebsiella pneumoniae | 2 | 2 to 4 | 0.5 to 16 | 2 to >16 | Pos | Pos | Pos(1); Neg(1) | Neg(2) |
| co-producing (3) | | | | | | | | | |
| KPC/OXA (2) | Klebsiella pneumoniae | 2 | 4 to 16 | 4 to >16 | 8 to >16 | Pos | Pos | Pos | Pos-A |
| NDM/OXA (1) | Klebsiella pneumoniae | 1 | 4 | 4 | 16 | Pos | Pos | Pos-B | Pos-B |
| non-CPE (154) | | | | | | | | | |
| non-CP-CRE (48) | Citrobacter freundii | 1 | 1 | 0.5 | 2 | Neg | Neg | Neg | Neg |
| | Enterobacter amnigenus | 4 | 8 to 16 | 2 to 8 | 16 to >16 | Neg | Neg | Neg | Neg |
| | Enterobacter cloacae | 10 | 0.5 to >16 | ≤0.25 to >16 | 2 to 16 | Neg | Neg | Neg | Pos-A(1); Neg(9) |
| | Escherichia coli | 8 | 0.5 to 16 | ≤0.25 to 8 | 4 to >16 | Neg | Neg | Neg | Neg |
| | Klebsiella aerogenes | 3 | 1 to >16 | 0.5 to 16 | 4 to >16 | Neg | Neg | Neg | Neg |
| | Klebsiella pneumoniae | 22 | 0.5 to 16 | 0.5 to 8 | 4 to >16 | Neg | Neg | Neg | Neg |
| ESBL-producer (53) | | | | | | | | | |
| CTX-M (53) | Escherichia coli | 29 | ≤0.25 to 1 | ≤0.25 to 1 | ≤0.125 to 1 | Neg | Ind(2); Neg(27) | Neg | Neg |

TABLE 2-continued

| | | No. of isolates | MICs (µg/ml) | | | Fluore result | mCIM result | CNP result | CIT result |
|---|---|---|---|---|---|---|---|---|---|
| | | | Carbapenemase class and gene | | | | | | |
| | Species | No. of isolates | IPM | MEM | ERT | Fluore result | mCIM result | CNP result | CIT result |
| non-producer (53) | Klebsiella pneumoniae | 24 | =0.25 to 1 | ≤=0.25 | ≤=0.125 to 1 | Neg | Ind(2); Neg(22) | Neg | Neg |
| | Escherichia coli | 32 | =0.25 to 0.5 | ≤=0.25 | ≤=0.125 | Neg | Neg | Neg | Neg |
| | Klebsiella pneumoniae | 21 | =0.25 to 1 | ≤=0.25 | ≤=0.125 | Neg | Neg | Neg | Neg |

Abbreviations: CPE, carbapenemase-producing Enterobacteriaceae; ESBL, extended-spectrum-β-lactamase; MIC, minimum inhibitory concentration; IPM, imipenem; MEM, meropenem; ERT, ertapenem; Fluore, fluorogenic assay; mCIM, modified carbapenem inactivation method; CNP, Carba NP test; CIT, carbapenemase inhibition test.

Abbreviations: Pos, positive; Neg, negative; Ind, indeterminate; Pos-A, Ambler class A carbapenemase detected; Pos-B, metallo-β-lactamase detected.

INDUSTRIAL APPLICABILITY

The present disclosure relates to a novel compound capable of detecting beta-lactamase and carbapenemase. The compound can detect beta-lactamase and carbapenemase with high sensitivity and, therefore, can be applied to various biochemical researches. In addition, the compound can clinically detect antibiotic-resistant bacteria and can be usefully used for in-vitro diagnosis of antibiotic-resistant bacterial infectious diseases.

The invention claimed is:

1. A compound selected from the group consisting of the following compounds;

[Compound OMCL01203]

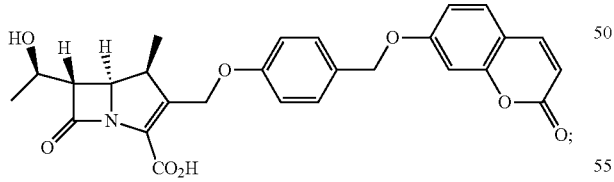

[Compound OMCL01204]

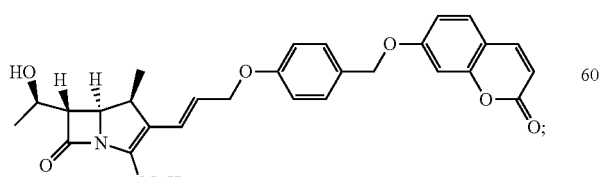

[Compound OMCL01205]

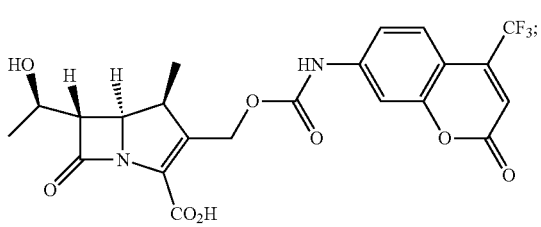

[Compound OMCL01206]

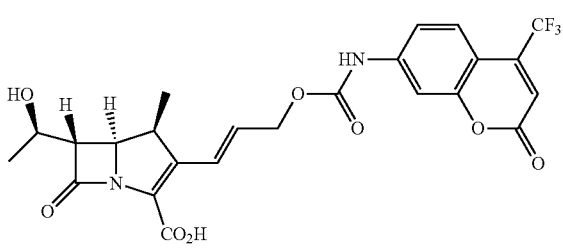

[Compound OMCL01207]

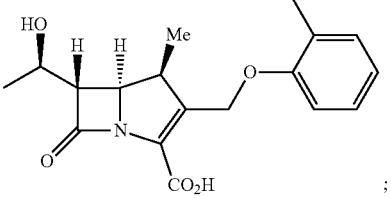

; and

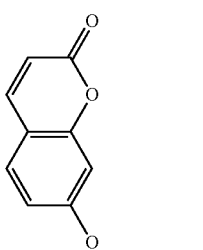

-continued
[Compound OMCL01208]
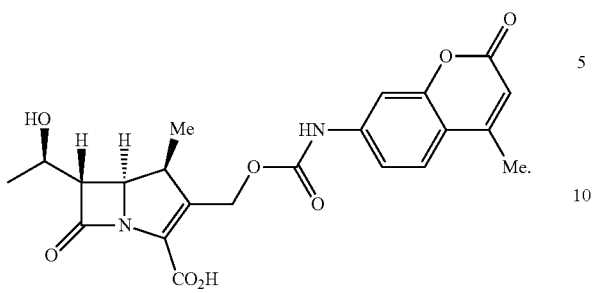
2. A compound represented by the following Chemical Formula:
[Compound OMCL01209]
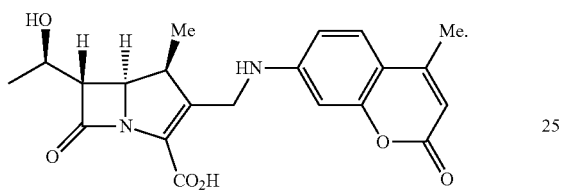
* * * * *